United States Patent [19]

Walker

[11] 4,288,384

[45] Sep. 8, 1981

[54] N-CYANOALKYL HALOACETAMIDES HERBICIDAL ANTIDOTES

[75] Inventor: Francis H. Walker, Mill Valley, Calif.

[73] Assignee: Stauffer Chemical Company, Westport, Conn.

[21] Appl. No.: 73,392

[22] Filed: Sep. 7, 1979

[51] Int. Cl.³ .................. C07C 121/46; C07C 121/14
[52] U.S. Cl. ................................ 260/464; 260/465.4; 260/465 D; 71/88; 71/94; 71/95; 71/100; 71/105; 71/111; 71/118
[58] Field of Search ........................... 260/465.4, 464; 424/304; 71/105

[56] References Cited

U.S. PATENT DOCUMENTS

| | | | |
|---|---|---|---|
| 3,145,230 | 8/1964 | Speziale et al. | 260/464 |
| 3,923,494 | 12/1975 | Teach | 260/465.4 |
| 3,966,789 | 6/1976 | Oishi et al. | 260/465.4 |
| 4,021,224 | 5/1977 | Pallos et al. | 71/88 |
| 4,124,376 | 11/1978 | Pallos et al. | 71/118 |

FOREIGN PATENT DOCUMENTS 516186 12/1952 Belgium ............................. 260/464

OTHER PUBLICATIONS

Gaughan et al., "Herbicide Composition Containing, etc."; (1977) CA 86 No. 151516z. (1977).
Japan Soda "Preparation of N-cyanoalkylhaloacetamides." (1967) CA 67 No. 108253g. (1967).
Nakamura, "Comparison of Effects of Fungicides, etc."; (1975) CA 85 No. 57853q. (1976).
Hamm et al., "Effect of Variations in the Acyl, etc." (1957) J. Ag. and Food Chem. 5 pp. 30-32 (1957).

Primary Examiner—Glennon H. Hollrah
Attorney, Agent, or Firm—Harry A. Pacini

[57] ABSTRACT

Compounds having the formula

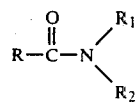

in which
R is 1-4 carbon haloalkyl;
R₁ is selected from the group consisting of hydrogen and 1-4 carbon alkyl; and
R₂ is selected from the group consisting of 2-8 carbon cyanoalkyl, 5-12 carbon cyanoalkylcycloalkyl, 5-12 carbon cyanocycloalkyl, 3-6 carbon cyanoalkylalkoxy, and cyanobenzyl;
provided that when R₂ is cyanoalkyl, R is dibromoalkyl, are useful for the protection of crops from thiocarbamate and haloacetanilide herbicidal injury.

39 Claims, No Drawings

N-CYANOALKYL HALOACETAMIDES HERBICIDAL ANTIDOTES

BACKGROUND OF THE INVENTION

Use of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control may increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and postemergence treatment of the plant and soil.

The most important determinant of herbicidal effectiveness is the susceptibility of the target weed pest. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations including particular weed susceptibility and overall cost limitations.

Need for Herbicidal Antidotes

Unfortunately, few herbicides are selective exclusively of weed species. Many are toxic to both weeds and the intended crop beneficiary. Therefore, a particular herbicide's use may be proscribed by its injurious effect on the cultivated crop even though it may otherwise provide excellent control of weeds plaguing that crop.

To preserve the beneficial aspects of herbicide use and to mitigate crop damage, many herbicidal antidotes have been prepared. These antidotes reduce or eliminate damage to the crop without substantially impairing the ameliorative effect of the herbicide. See U.S. Pat. No. 4,021,224 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist.

As used herein, "antidote" describes a compound which has the effect of establishing herbicidal selectivity.

DESCRIPTION OF THE INVENTION

It has now been discovered that certain N-cyanoalkyl-haloacetamide compounds are effective as antidotes for the protection of crops from thiocarbamate and haloacetanilide herbicidal injury. These compounds have the formula $$R-\overset{\overset{\displaystyle O}{\|}}{C}-N\diagdown_{R_2}^{R_1}$$

in which
- R is 1–4 carbon haloalkyl;
- $R_1$ is selected from the group consisting of hydrogen and 1–4 carbon alkyl; and
- $R_2$ is selected from the group consisting of 2–8 carbon cyanoalkyl, 5–12 carbon cyanoalkylcycloalkyl, preferably 6–9 carbon cyanoalkylcycloalkyl, 5–12 carbon cyanocycloalkyl, preferably 6–8 carbon cyanocycloalkyl, 3–6 carbon cyanoalkylalkoxy, and cyanobenzyl;
- provided that when $R_2$ is cyanoalkyl, R is dibromoalkyl.

This invention includes a two-part herbicidal system comprising (a) an antidotally effective amount of a compound of the formula $$R-\overset{\overset{\displaystyle O}{\|}}{C}-N\diagdown_{R_2}^{R_1}$$

in which
- R is 1–4 carbon haloalkyl;
- $R_1$ is selected from the group consisting of hydrogen and 1–4 carbon alkyl; and
- $R_2$ is selected from the group consisting of 2–8 carbon cyanoalkyl, 5–12 carbon cyanoalkylcycloalkyl, preferably 6–9 carbon cyanoalkylcycloalkyl, 5–12 carbon cyanocycloalkyl, preferably 6–8 carbon cyanocycloalkyl, 3–6 carbon cyanoalkylalkoxy, and cyanobenzyl;
- provided that when $R_2$ is cyanoalkyl, R is dibromoalkyl; and (b) an herbicidally effective amount of a thiocarbamate of the formula $$\underset{R_4}{\overset{R_3}{\diagdown}}N-\overset{\overset{\displaystyle O}{\|}}{C}-S-R_5$$

in which
- R is selected from the group consisting of 1–6 carbon alkyl and 2–6 carbon alkenyl;
- $R_4$ is selected from the group consisting of 1–6 carbon alkyl, 2–6 carbon alkenyl, cyclohexyl and phenyl; or
- $R_3$ and $R_4$ together form a 5–10 carbon alkylene ring; and
- $R_5$ is selected from the group consisting of 1–6 carbon alkyl, 1–4 carbon haloalkyl, 5–10 carbon alkylene ring, phenyl, substituted phenyl, wherein the substituents are 1–4 carbon alkyl, 1–4 carbon haloalkyl, and halo, benzyl and substituted benzyl, wherein the substituents are 1–4 carbon alkyl, 1–4 carbon haloalkyl, and halo.

In another embodiment, the invention includes
(a) an antidotally effective amount of a compound of the formula

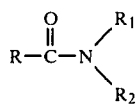

in which

R is 1-4 carbon haloalkyl;

$R_1$ is selected from the group consisting of hydrogen and 1-4 carbon alkyl; and $R_2$ is selected from the group consisting of 2-8 carbon cyanoalkyl, 5-12 carbon cyanoalkylcycloalkyl, preferably 6-9 carbon cyanoalkylcycloalkyl, 5-12 carbon cyanocycloalkyl, preferably 6-8 carbon cyanocycloalkyl, 3-6 carbon cyanoalkylalkoxy, and cyanobenzyl;

provided that when $R_2$ is cyanoalkyl, R is dibromoalkyl; and (b) an herbicidally effective amount of a haloacetanilide of the formula

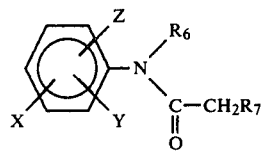

in which

X, Y, and Z are independently selected from the group consisting of hydrogen and 1-4 carbon alkyl;

$R_6$ is selected from the group consisting of 1-6 carbon alkyl, 2-10 carbon alkoxyalkyl, 3-6 carbon alkoxycarbonylalkyl, and dioxolan; and $R_7$ is selected from the group consisting of chlorine, bromine and iodine.

This invention lso includes the method of controlling undesirable vegetation while reducing herbicidal injury to crops which comprises applying to the locus where control is desired an antidotally effective amount of a compound of the formula

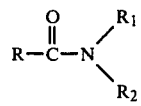

in which

R is 1-4 carbon haloalkyl;

$R_1$ is selected from the group consisting of hydrogen and 1-4 carbon alkyl; and $R_2$ is selected from the group consisting of 2-8 carbon cyanoalkyl, 5-12 carbon cyanoalkylcycloalkyl, preferably 6-9 carbon cyanoalkylcycloalkyl, 5-12 carbon cyanocycloalkyl, preferably 6-8 carbon cyanocycloalkyl, 3-6 carbon cyanoalkylalkoxy, and cyanobenzyl;

provided that when $R_2$ is cyanoalkyl, R is dibromoalkyl.

The terms "alkyl," and "alkenyl" as used herein are intended to include both straight- and branched-chain groups. All carbon atom ranges are intended to be inclusive of both upper and lower limits. The term "halo" includes mono- and polyhalogen compounds.

Preparation

N-cyanoalkyl-haloacetamides can be prepared by a two step process.

I. In the first step a nitrile amine is prepared by slowly adding an aqueous solution of potassium cyanide to a mixture of a ketone, ammonium chloride, and ether. Temperature during the addition is maintained at 5°-10° C. The mixture was then stirred for 10-20 hours at room temperature.

The amine product may be isolated by any standard procedure, such as separating the ether layer, extracting the aqueous layer with additional ether, and combining the ether solution. Following evaporation of the ether solution, the product is purified by distillation.

Alternatively, the amine may be recovered by passing hydrogen chloride gas into the ether solution so that the product separates as an insoluble hydrochloride salt which is removed by filtration.

Methylaminonitrile is prepared in the same general manner utilizing methylamine hydrochloride in place of ammonium chloride.

II. A molar amount of the nitrile amine, prepared in Step I, is used to make a solution with equimolar amounts of an acid acceptor, such as triethyl amine or aqueous sodium hydroxide, in a suitable solvent, such as dichloromethane. An equimolar amount of halogenated acid chloride is slowly added to this solution while the temperature of the solution is maintained between 10°-15° C.

In some cases it is convenient to use the hydrochloride salt of the amine. In such cases 2 moles of caustic are used per mole of acid chloride.

The N-cyanoalkyl-haloacetamide product, isolated by evaporation of the solvent, is purified by recrystallization from a suitable solvent, such as hexane.

Examples of the preparation of specific compounds of this invention follow. (Compound numbers denote the compounds appearing in Tables I, IV, and V.)

EXAMPLE 1

(Compound No. 3)

Preparation of N-(1-cyano-1,2-dimethylpropyl)-2,3-Dibromopropionamide

I. The reactant 2,3-dimethyl-2-aminobutyronitrile hydrochloride was prepared by the following reaction. A solution of 136 grams (g) (2.1 moles) of potassium cyanide in 220 milliliters (ml) of water was added dropwise at 10°-15° C. to a mixture of 172.2 g (2.0 moles) of 3-methyl-2-butanone, 110.2 g (2.1 moles) ammonium chloride, and 300 ml of ether. The mixture was allowed to reach room temperature at which it was stirred overnight.

The mixture was filtered and the filtrate phase separated. The aqueous layer was extracted with three 200 ml portions of ether. The ether solutions were combined and dried over magnesium sulfate. The amine was isolated by passing anhydrous hydrogen chloride gas through the solution until separation of solid ceased. The hydrochloride was separated by filtration and vacuum dried to give 85.7 g of 2,3-dimethyl-2-aminopropionitrile hydrochloride (m.p./decomposition 115° C.).

II. A mixture of 4.5 g (0.03 mole) of the 2,3-dimethyl-2-aminobutyronitrile hydrochloride, 4.8 g (0.06 mole) of 50% aqueous sodium hydroxide, 15 ml of dichloromethane and 15 ml of water was prepared. A second solution of 7.5 g (0.03 mole) of 2,3-dibromopropionyl chloride in 15 ml dichloromethane was added with rapid stirring to the first mixture at 10°–15° C. The mixture was then allowed to reach room temperature.

The product was isolated by washing the reaction mixture with water, separating the organic layer, and drying over magnesium sulfate. The 5.3 g of product, remaining after evaporation of the solvent, was purified by recrystallization from aqueous ethanol. This yielded 3.5 g of solid N-(1-cyano-1,2-dimethylpropyl)-2,3-dibromopropionamide (m.p. 131°–133° C.). Structure was confirmed by nuclear magnetic resonance spectroscopy (NMR).

EXAMPLE 2

(Compound No. 7)

Preparation of N-(1-cyano-1-cyclopropyl) ethyl dichloroacetamide

I. The reactant 2-amino-2-cyclopropylpropionitrile was prepared as follows. A solution of 41.0 g (0.63 mole) of potassium cyanide in 65 ml of water was added dropwise with rapid stirring at 10°–15° C. to a mixture of 50.0 g (0.59 mole) of methyl cyclopropyl ketone, 32.5 g (0.61 mole) of ammonium chloride, and 60 ml of ether. The mixture was allowed to come to room temperature and stirred overnight.

The mixture was then filtered. Following separation of the filtrate phase, the aqueous layer was extracted with two 100 ml portions of ether. The ether solutions were combined and dried over magnesium sulfate. The ether was removed by distillation at atmospheric pressure. The residue was vacuum distilled at 15 mm to yield 20.1 g of 2-amino-2-cyclopropylpropionitrile (b.p. 72°–77° C., $n_D^{30}$ 1.4505).

II. A solution of 5.9 g (9.04 mole) dichloroacetylchloride in 15 ml dichloromethane was added dropwise with rapid stirring at 10°–15° C. to a mixture of 3.9 g (0.04 mole) of the 2-amino-2-cyclopropylpropronitrile, 3.2 g (0.04 mole) of 50% aqueous sodium hydroxide, 75 ml of dichloromethane, and 15 ml of water. The mixture was allowed to reach room temperature.

The product was isolated by washing the reaction mixture with 100 ml of water, separating the organic layer, and drying over magnesium sulfate. Evaporation of the solvents yielded 8.0 g of N-(1-cyano-1-cyclopropyl)ethyl dichloroacetamide (m.p. 97°–100° C.). Structure was confirmed by NMR.

EXAMPLE 3

(Compound No. 15)

Preparation of N-methyl-N-(1-cyanocyclopentyl)trichloroacetamide

I. A solution of 68 g (1.04 mole) of potassium cyanide in 110 ml of water was added dropwise at 10°–15° C. to a mixture of 84.7 g (1.00 mole) of cyclopentanone, 69.4 g (1.03 moles) of methylamine hydrochloride, and 150 ml of ether. The mixture was allowed to reach room temperature at which it was stirred overnight.

The mixture was filtered and the filtrate phase was separated. The aqueous layer was extracted with three 200 ml portions of ether. The ether solutions were combined and dried over magnesium sulfate. Removal of the ether by vacuum evaporation yielded 108.5 g of product which was purified by distillation to yield 83 g of 1-methylaminocyclopentancarbonitrile (b.p. 61°–62° C./0.7 mm, $n_D^{30}$ 1.4598).

II. A solution of 7.3 g (0.04 mole) trichloroacetylchloride in 20 ml of ether was slowly added with rapid stirring at 10°–15° C. to a mixture of 6.2 g (0.05 mole) of the 1-methylaminocyclopentanecarbonitrile and 4.0 g (0.04 mole) of triethylamine in 80 ml ether. After reaching room temperature the mixture was filtered. The filtrate was evaporated and recrystallized from hexane, yielding 1.0 g of N-methyl-N-(1-cyclopentanecarbonitrile) trichloroacetamide (m.p. 101°–105° C.). Structure was confirmed by NMR.

EXAMPLE 4

(Compound No. 30)

Preparation of N-(1-cyano-1-cyclohexyl)ethyl dichloroacetamide

I. A solution of 29.0 g (0.45 mole) of potassium cyanide in 45 ml of water was added dropwise with stirring at 10°–15° C. to a mixture of 50.0 g (0.40 mole of cyclohexylethanone, 23 g (0.43 mole) of ammonium chloride and 60 ml of ether. The mixture was allowed to reach room temperature at which it was stirred overnight.

The mixture was then filtered. After separation of the filtrate phase, the aqueous layer was extracted with three 40 ml portions of ether. The ether solutions were combined and dried over magnesium sulfate. The product was isolated by passing anhydrous hydrogen chloride gas through the solution until separation of the solid ceased. The hydrochloride was separated by filtration and vacuum dried to give 5.3 g of 2-amino-2-cyclohexylpropionitrile hydrochloride reactant (m.p. 145°–147° C./decomposed).

II. A solution of 4.5 g (0.03 mole) dichloroacetylchloride in 15 ml dichloromethane was slowly added with rapid stirring at 10°–15° C. to a mixture of 5.3 g (0.03 mole) of the 2-amino-2-cyclohexylpropionitrile hydrochloride, 4.8 g (0.06 mole) of 50% aqueous sodium hydroxide, 75 ml of dichloromethane, and 15 ml of water. The mixture was allowed to reach room temperature.

The product was isolated by washing the reaction mixture with water, separating the organic layer, and drying over magnesium sulfate. Evaporation of the solvent yielded 2.0 g of N-(1-cyano-1-cyclohexyl)ethyl-dichloroacetamide (m.p. 109°–114° C.). Structure was confirmed by NMR.

Examples of compounds typical of this invention appear in Table I.

TABLE I

N-CYANOALKYL-HALOACETAMIDES $$R-\overset{\overset{O}{\|}}{C}-N\overset{R_1}{\underset{R_2}{}}$$

| Cmpd. No. | R | R₁ | R₂ | Chemical Name | Physical Constant |
|---|---|---|---|---|---|
| 1 | BrCH₂CH(Br) | H | C(CH₃)₂CN | N-dimethylacetonitrilo-2,3-dibromopropionamide | m.p. 134–137° C. |
| 2 | BrCH₂CH(Br) | CH₃ | C(CH₃)₂CN | N-methyl-N-dimethylacetonitrilo-2,3-dibromopropionamide | $n_D^{30}$ 1.5146 |
| 3 | BrCH₂CH(Br) | H | CH₃, CCH(CH₃)₂, CN | N-(1-cyano-1',2'-dimethylpropyl)2,3-dibromopropionamide | m.p. 131–133° C. |
| 4 | BrCH₂CH(Br) | H | CH₃, CCH₂OCH₃, CN | N-(1-cyano-1-methyl-2-methoxyethyl)2,3-dibromopropionamide | $n_D^{30}$ 1.5157 |
| 5 | BrCH₂CH(Br) | CH(CH₃)₂ | CH₂CN | N-isopropyl-N-cyanomethyl-2,3-dibromopropionamide | $n_D^{30}$ 1.5250 |
| 6 | ClCH₂ | H | CN, C(CH₃)-cyclopropyl | N-(1-cyano-1-cyclopropylethyl)-chloroacetamide | $n_D^{30}$ 1.4874 |
| 7 | Cl₂CH | H | CN, C(CH₃)-cyclopropyl | N-(1-cyano-1-cyclopropylethyl)-dichloroacetamide | m.p. 97–100° C. |
| 8 | BrCH₂CH(Br) | H | CN, C(CH₃)-cyclopropyl | N-(1-cyano-1-cyclopropylethyl)-2,3-dibromopropionamide | waxy solid |
| 9 | ClCH₂ | H | 1-cyanocyclopentyl | N-(1-cyanocyclopentyl)chloroacetamide | m.p. 70–73° C. |
| 10 | ClCH₂ | CH₃ | 1-cyanocyclopentyl | N-methyl-N-(1-cyanocyclopentyl)chloroacetamide | m.p. 42–46° C. |
| 11 | BrCH₂ | CH₃ | 1-cyanocyclopentyl | N-methyl-N-(1-cyanocyclopentyl)bromoacetamide | low melting solid |
| 12 | ClCH₂CH(Cl) | H | 1-cyanocyclopentyl | N-(1-cyanocyclopentyl)-2,3-dichloropropionamide | semi-solid |
| 13 | Cl₂CH | H | 1-cyanocyclopentyl | N-(1-cyanocyclopentyl)dichloroacetamide | m.p. 95–98° C. |
| 14 | Cl₂CH | CH₃ | 1-cyanocyclopentyl | N-methyl-N-(1-cyanocyclopentyl)-dichloroacetamide | m.p. 56–60° C. |
| 15 | Cl₃C | CH₃ | 1-cyanocyclopentyl | N-methyl-N-(1-cyanocyclopentyl)trichloroacetamide | m.p. 101–105° C. |
| 16 | BrCH₂CH(Br) | H | 1-cyanocyclopentyl | N-(1-cyanocyclopentyl)-2,3-dibromopropionamide | m.p. 140–143° C. |
| 17 | BrCH₂CH(Br) | CH₃ | 1-cyanocyclopentyl | N-methyl-N-(1-cyanocyclopentyl)2,3-dibromopropionamide | low melting solid |
| 18 | CH₃CH(Br)CH(Br) | H | 1-cyanocyclopentyl | N-(1-cyanocyclopentyl)-2,3-dibromobutyramide | m.p. 110–117° C. |
| 19 | ClCH₂ | H | CN, CH-cyclopentyl | N-(1-cyclopentylacetonitrilo)-chloroacetamide | $n_D^{30}$ 1.4977 |

TABLE I-continued
N-CYANOALKYL-HALOACETAMIDES $$R-\underset{\underset{O}{\|}}{C}-N\underset{R_2}{\overset{R_1}{<}}$$

| Cmpd. No. | R | R₁ | R₂ | Chemical Name | Physical Constant |
|---|---|---|---|---|---|
| 20 | Cl₂CH | H | CN–CH–(cyclopentyl) | N-(1-cyclopentylacetonitrilo)-dichloroacetamide | $n_D^{30}$ 1.5035 |
| 21 | Cl₂CH | H | CN–C(CH₃)–(cyclopentyl) | N-(1-methyl-1-cyclopentylacetonitrilo)-dichloroacetamide | $n_D^{30}$ 1.4990 |
| 22 | BrCH₂CH(Br) | H | CN–CH–(cyclopentyl) | N-(1-cyclopentylacetonitrilo)-2,3-dibromopropionamide | $n_D^{30}$ 1.5238 |
| 23 | ClCH₂ | H | 1-cyanocyclohexyl | N-(1-cyanocyclohexyl)chloroacetamide | m.p. 128–129° C. |
| 24 | ClCH₂ | CH₃ | 1-cyanocyclohexyl | N-methyl-N-(1-cyanocyclohexyl)chloroacetamide | m.p. 75–79° C. |
| 25 | BrCH₂ | H | 1-cyanocyclohexyl | N-(1-cyanocyclohexyl)bromoacetamide | m.p. 96–99° C. |
| 26 | Cl₂CH | H | 1-cyanocyclohexyl | N-(1-cyanocyclohexyl)dichloroacetamide | m.p. 124–126° C. |
| 27 | Cl₂CH | CH₃ | 1-cyanocyclohexyl | N-methyl-N-(1-cyanocyclohexyl)-dichloroacetamide | m.p. 108–111° C. |
| 28 | Cl₃C | H | 1-cyanocyclohexyl | N-(1-cyanocyclohexyl)-trichloroacetamide | m.p. 135–139° C. |
| 29 | BrCH₂CH(Br) | H | 1-cyanocyclohexyl | N-(1-cyanocyclohexyl)-2,3-dibromopropionamide | m.p. 100° C. |
| 30 | Cl₂CH | H | CN–C(CH₃)–(cyclohexyl) | N-(1-cyano-1-cyclohexyl)ethyl dichloroacetamide | m.p. 109–114° C. |
| 31 | ClCH₂ | H | 1-cyano-4-methylcyclohexyl | N-(1-cyano-4-methylcyclohexyl)chloroacetamide | m.p. 77–80° C. |
| 32 | Cl₂CH | H | 1-cyano-4-methylcyclohexyl | N-(1-cyano-4-methylcyclohexyl)dichloroacetamide | m.p. 118–121° C. |
| 33 | CH₃CHCH₂(Br) | H | 1-cyano-4-methylcyclohexyl | N-(1-cyano-4-methylcyclohexyl)-2-bromopropionamide | m.p. 116–119° C. |
| 34 | Cl₃C | H | 1-cyano-4-methylcyclohexyl | N-(1-cyano-4-methylcyclohexyl)-trichloroacetamide | m.p. 132–135° C. |
| 35 | ClCH₂CH(Cl) | H | 1-cyano-4-methylcyclohexyl | N-(1-cyano-4-methylcyclohexyl)-2,3-dichloropropionamide | m.p. 90–100° C. |
| 36 | BrCH₂CH(Br) | H | 1-cyano-4-methylcyclohexyl | N-(1-cyano-4-methylcyclohexyl)-2,3-dibromopropionamide | m.p. 155–158° C. |
| 37 | ClCH₂CCl₂ | H | 1-cyano-4-methylcyclohexyl | N-(1-cyano-4-methylcyclohexyl)-2,2,3-trichloropropionamide | m.p. 90–97° C. |
| 38 | ClCH₂ | H | 1-cyano-4-ethylcyclohexyl | N-(1-cyano-4-ethylcyclohexyl)-chloroacetamide | m.p. 98–100° C. |

TABLE I-continued
N-CYANOALKYL-HALOACETAMIDES $$R-\overset{O}{\underset{\|}{C}}-N\overset{R_1}{\underset{R_2}{<}}$$

| Cmpd. No. | R | $R_1$ | $R_2$ | Chemical Name | Physical Constant |
|---|---|---|---|---|---|
| 39 | $BrCH_2$ | H | 4-$C_2H_5$-1-CN-cyclohexyl | N-(1-cyano-4-ethylcyclohexyl)-bromoacetamide | m.p. 96–99° C. |
| 40 | $Cl_2CH$ | H | 4-$C_2H_5$-1-CN-cyclohexyl | N-(1-cyano-4-ethylcyclohexyl)-dichloroacetamide | m.p. 153–156° C. |
| 41 | $BrCH_2\overset{Br}{\underset{|}{C}}H$ | H | 4-$C_2H_5$-1-CN-cyclohexyl | N-(1-cyano-4-ethylcyclohexyl)-2,3-dibromopropionamide | m.p. 139–143° C. |
| 42 | $ClCH_2$ | H | 4-$C(CH_3)_3$-1-CN-cyclohexyl | N-(1-cyano-4-t-butylcyclohexyl)-chloroacetamide | m.p. 129–132° C. |
| 43 | $BrCH_2$ | H | 4-$C(CH_3)_3$-1-CN-cyclohexyl | N-(1-cyano-4-t-butylcyclohexyl)-bromoacetamide | m.p. 128–121° C. |
| 44 | $Cl_2CH$ | H | 4-$C(CH_3)_3$-1-CN-cyclohexyl | N-(1-cyano-4-t-butylcyclohexyl)-dichloroacetamide | m.p. 175–180° C. |
| 45 | $BrCH_2\overset{Br}{\underset{|}{C}}H$ | H | 4-$C(CH_3)_3$-1-CN-cyclohexyl | N-(1-cyano-4-t-butylcyclohexyl)-2,3-dibromopropionamide | m.p. 160–163° C. |
| 46 | $ClCH_2$ | H | 4-$CH_2C(CH_3)_3$-1-CN-cyclohexyl | N-(1-cyano-4-neopentyl-cyclohexyl-chloroacetamide | m.p. 81–95° C. |
| 47 | $ClCH_2$ | H | 1-CN-cycloheptyl | N-(1-cyanocycloheptyl)-chloroacetamide | m.p. 90–91° C. |
| 48 | $Cl_2CH$ | H | 1-CN-cycloheptyl | N-(1-cyanocycloheptyl)dichloroacetamide | m.p. 89–90° C. |
| 49 | $Cl_3C$ | H | 1-CN-cycloheptyl | N-(1-cyanocycloheptyl)trichloroacetamide | m.p. 78–79° C. |
| 50 | $BrCH_2\overset{Br}{\underset{|}{C}}H$ | H | 1-CN-cycloheptyl | N-(1-cyanocycloheptyl)-2,3-dibromopropionamide | m.p. 123–126° C. |
| 51 | $Cl_2CH$ | H | 1-CN-cyclooctyl | N-(1-cyanocyclooctyl)dichloroacetamide | m.p. 128–130° C. |
| 52 | $BrCH_2\overset{Br}{\underset{|}{C}}H$ | H | 1-CN-cyclooctyl | N-(1-cyanocyclooctyl)-2,3-dibromopropionamide | m.p. 128–131° C. |
| 53 | $ClCH_2$ | H | $\overset{CN}{\underset{|}{C}}H{-}C_6H_5$ | N-(1-cyanobenzyl)chloroacetamide | m.p. 90–92° C. |
| 54 | $ClCH_2$ | $CH_3$ | $\overset{CN}{\underset{|}{C}}H{-}C_6H_5$ | N-methyl-N-(1-cyanobenzyl)chloroacetamide | $n_D^{30}$ 1.5444 |
| 55 | $Cl_2CH$ | H | $\overset{CN}{\underset{|}{C}}H{-}C_6H_5$ | N-(1-cyanobenzyl)dichloroacetamide | decomposed above 80° C. |

TABLE I-continued

N-CYANOALKYL-HALOACETAMIDES $$R-\underset{\underset{}{\overset{O}{\|}}}{C}-N\diagup^{R_1}_{\diagdown R_2}$$

| Cmpd. No. | R | $R_1$ | $R_2$ | Chemical Name | Physical Constant |
|---|---|---|---|---|---|
| 56 | $Cl_2CH$ | $CH_3$ | CN<br>\|<br>CH—⟨O⟩ | N-methyl-N-(1-cyanobenzyl) dichloroacetamide | $n_D^{30}$ 1.5490 |
| 57 | $Cl_3C$ | H | CN<br>\|<br>CH—⟨O⟩ | N-(1-cyanobenzyl)trichloro-acetamide | m.p. 75–80° C. |
| 58 | $Cl_3C$ | $CH_3$ | CN<br>\|<br>CH—⟨O⟩ | N-methyl-N-(1-cyanobenzyl) trichloroacetamide | $n_D^{30}$ 1.5508 |
| 59 | $BrCH_2$ | $CH_3$ | CN<br>\|<br>CH—⟨O⟩ | N-methyl-N-(1-cyanobenzyl) bromoacetamide | $n_D^{30}$ 1.5612 |
| 60 | Br<br>\|<br>$BrCH_2CH$ | $CH_3$ | CN<br>\|<br>CH—⟨O⟩ | N-methyl-N-(1-cyanobenzyl)-2,3-dibromopropionamide | m.p. 90–92° C. |

Testing

The thiocarbamates of the present compositions can be prepared by the procedures described in the United States Pat. Nos. 2,913,327, and 3,185,720. The haloacetanilide can be prepared by the procedures described in U.S. Pat. No. 3,442,945.

Stock solutions of the herbicides were prepared by diluting the requisite amount of each herbicide in water. The solution compositions and application rates and methods are summarized in Table II.

TABLE II

| | Herbicide Stock Solutions | | | | |
|---|---|---|---|---|---|
| | Composition | | Application | | |
| Herbicide Name | Herbicide (mg) | Water (ml) | Ml/ flat | lb/ acre | Method* |
| VERNAM® | | | | | |
| S-propyl N,N-dipropyl thio-carbamate | 390 | 400 | 5 | 1.00 | PPI |
| | 427 | 350 | 5 | 1.25 | PPI |
| | 2925 | 600 | 5 | 5.00 | PPI |
| | 1755 | 300 | 5 | 6.00 | PPI |
| | | | 5 | 7.00 | PPI |
| EPTAM® S-ethyl-N,N-dipropyl thio-carbamate | | | 5 | 5.00 | PPI |
| SUTAN® S-ethyl diisobutyl-thiocarbamate | 1040 | 200 | 5 | 5.00 | PPI |
| RO-NEET® S-ethyl N-ethyl N-cyclohexyl thio-carbamate | 780 | 250 | 5 | 3.00 | PPI |
| LASSO® 2-chloro-2',6'-diethyl-N-(methoxy-methyl) acetanilide | 1875 | 150 | 2 | 3.00 | PES |
| | 2500 | 150 | 2 | 4.00 | PES |

*See explanation of abbreviations at the end of Table III.

Stock solutions of each antidote compound were prepared at the desired concentrations by diluting the requisite amounts of each antidote in acetone. The compositions and rates for each method of application are summarized in Table III.

TABLE III

| Antidote Stock Solutions | | | | |
|---|---|---|---|---|
| Antidote: N-cyanoalkyl-haloacetamide | | | | |
| Composition | | Application | | |
| Antidote (mg) | Acetone (ml) | ml/flat | lb/acre | Method* |
| 95 | 15 | 0.30 | 1.00 | IF |
| 95 | 15 | 1.50 | 5.00 | IF |
| 40 | 40 | 1.00 | 0.25 | PPI |
| 16 | 20 | 2.50 | 0.50 | PPI |
| 40 | 20 | 2.00 | 1.00 | PPI |
| 40 | 20 | 4.00 | 2.00 | PPI |
| 95 | 15 | 3.00 | 5.00 | PPI |
| 95 | 15 | 3.00 | 5.00 | PES |

*IF = In-furrow surface application.
PPI = Pre-plant incorporation of herbicide and antidote as a tank mix.
PES = Preemergence surface application.

All of the soil used in the tests described herein was loamy sand oil treated with 50 parts per million (ppm) each of a commercially available fungicide, cis-N[tri-chloromethyl)thio]-4-cyclohexene-1,2-dicarboximide, and an 18-18-18 fertilizer which contains 18% by weight equivalent each of nitrogen, phosphorus pentoxide, and potassium oxide.

The thiocarbamate herbicides were applied to the soil by pre-plant incorporation. The acetanilide was applied by atomizing the herbicide or herbicidal antidote tank mix to the soil surface of seeded flats.

For in-furrow (IF) antidote applications, a one pint (473 cubic centimeters) sample of soil from each planting flat was removed and retained. After leveling and furrowing the soil, seeds of the crop or weed species were planted ½ inch deep (1.27 cm). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

For the pre-plant incorporation (PPI) method the herbicide and the antidote of each test group were incorporated into the soil as a tank mix using a five gallon rotary mixer.

Pre-emergence surface (PES) application involves spraying the soil-covered seeds after planting.

All flats were placed on greenhouse benches where temperature was maintained between 70° and 90° F. (21.1° to 32.2° C.). The flats were watered by sprinkling as needed to assure good plant growth.

Control flats contaied crops treated with herbicides only at the various rates and methods of application.

Injury ratings were taken four weeks after application of antidote. The effectiveness of the antidote was determined by visual comparison of injuries to crops and weeds in the control of test flats to those in untreated flats.

The treated crops initially screened for diminution of herbicidal injury were milo, wheat, cotton, rice, barley, corn, and soybeans. Those componds which showed substantial crop injury reduction were further tested at reduced rates. The herbicides and antidote compositions were then screened on at least two weed species. The weed species tested for control included watergrass (*Echinochloa crusgalli*), foxtail (*Setaria viridis*), wild oat (*Avena fatua*), Johnsongrass (*Sorghum halepense*), and shattercane (*Sorghum bicolor*).

KEY TO TABLES IV AND V

Compound numbers in these tables correspond to the numbers and their chemical description in Table I.

Those compounds omitted in Table V were not tested on weed species.

Application:
 IF—In-furrow surface
 PPI—Pre-plant incorporation of herbicide and antidote as a tank mix except for VERNAM and the antidotes which were separately incorporated
 PES—Pre-emergence surface Herbicides VERNAM ®—S-propyl N,N-dipropylthiocarbamate
EPTAM ®—S-ethyl N,N-dipropylthiocarbamate
SUTAN ®—S-ethyl diisobutylthiocarbamate
RO-NEET ®—S-ethyl N-ethyl-N-cyclohexylthiocarbamate
LASSO ®—2-chloro-2',6'-diethyl-N-(methoxymethyl) acetanilide Rates: All rates are shown in pounds per acre.
Injury Ratings:
 U=Antidotally untreated; % injury 4 weeks after herbicide application.
 T=Antidotally treated; % injury 4 weeks after treatment with herbicide plus antidote compound.
 —=Indicates no change.

TABLE IV

Antidotal Effectiveness

| Antidote | | | Herbicide | | % Injury | | | | | | | | | | | | |
|---|---|---|---|---|---|---|---|---|---|---|---|---|---|---|---|---|---|
| Cmpd. No. | Rate | Method | Name | Rate | Milo U | Milo T | Wheat U | Wheat T | Cotton U | Cotton T | Rice U | Rice T | Barley U | Barley T | Corn U | Corn T | Soybean U | Soybean T |
| 1 | 5.00 | IF | VERNAM | 1.00 | 100 | — | 90 | — | 55 | 100 | 95 | — | 90 | 60 | | | | |
|  | 5.00 | IF | VERNAM | 6.00 | | | | | | | | | | | 70 | 0 | 30 | 100 |
|  | 1.00 | PPI | VERNAM | 6.00 | | | | | | | | | | | | | 60 | — |
|  | 5.00 | PPI | VERNAM | 6.00 | | | | | | | | | | | | | 60 | — |
|  | 1.00 | PPI | VERNAM | 6.00 | | | | | | | | | | | | | 60 | 30 |
|  | 5.00 | PPI | VERNAM | 6.00 | | | | | | | | | | | | | 60 | 40 |
|  | 0.50 | PPI | EPTAM | 5.00 | | | | | | | | | 80 | 40 | | | | |
|  | 5.00 | PPI | EPTAM | 5.00 | | | | | | | | | 80 | 60 | | | | |
|  | 1.00 | PPI | SUTAN | 5.00 | | | | | 35 | — | | | | | | | | |
|  | 5.00 | PPI | SUTAN | 5.00 | | | | | 35 | 50 | | | | | | | | |
| 2 | 5.00 | IF | VERNAM | 1.00 | 100 | — | 97 | — | | | 100 | — | | | | | | |
|  | 5.00 | IF | VERNAM | 5.00 | | | | | 80 | — | | | 97 | 60 | 65 | 60 | 5 | — |
|  | 5.00 | IF | VERNAM | 6.00 | | | | | | | | | | | | | 40 | — |
| 3 | 5.00 | IF | VERNAM | 1.00 | 100 | 30 | 95 | 40 | 60 | — | 95 | — | 90 | 20 | | | | |
|  | 5.00 | IF | VERNAM | 5.00 | | | | | | | | | | | 90 | 0 | 50 | 90 |
|  | 1.00 | IF | VERNAM | 1.00 | 80 | 40 | | | | | | | | | | | | |
|  | 5.00 | IF | VERNAM | 1.00 | 80 | 30 | | | | | | | | | | | | |
|  | 1.00 | IF | VERNAM | 1.25 | | | | | | | | | 80 | 10 | | | | |
|  | 5.00 | IF | VERNAM | 1.25 | | | | | | | | | 80 | 0 | | | | |
|  | 1.00 | PPI | VERNAM | 1.25 | | | 90 | 80 | | | | | | | | | | |
|  | 5.00 | PPI | VERNAM | 1.25 | | | 90 | 60 | | | | | | | | | | |
|  | 0.50 | PPI | VERNAM | 1.25 | | | | | | | | | 50 | 30 | | | | |
|  | 1.00 | PPI | VERNAM | 1.25 | | | | | | | | | 50 | — | | | | |
|  | 2.00 | PPI | VERNAM | 1.25 | | | | | | | | | 50 | — | | | | |
|  | 1.00 | IF | RO-NEET | 3.00 | 75 | 60 | | | | | | | | | | | | |
|  | 5.00 | IF | RO-NEET | 3.00 | 75 | 30 | | | | | | | | | | | | |
|  | 5.00 | PES | LASSO | 3.00 | 90 | 55 | 55 | 10 | | | | | | | | | | |
|  | 5.00 | PES | LASSO | 4.00 | | | | | | | | | 80 | 10 | | | | |
| 4 | 5.00 | IF | VERNAM | 1.00 | 100 | 70 | 85 | 70 | 60 | 100 | 100 | — | 80 | 40 | | | | |
|  | 5.00 | IF | VERNAM | 5.00 | | | | | | | | | | | 90 | 0 | 60 | 80 |
|  | 1.00 | IF | VERNAM | 1.25 | | | | | | | | | 80 | 50 | | | | |
|  | 5.00 | IF | VERNAM | 1.25 | | | | | | | | | 80 | 60 | | | | |
|  | 0.50 | PPI | VERNAM | 1.25 | | | | | | | | | 50 | — | | | | |
|  | 1.00 | PPI | VERNAM | 1.25 | | | | | | | | | 50 | — | | | | |
|  | 2.00 | PPI | VERNAM | 1.25 | | | | | | | | | 50 | — | | | | |
|  | 1.00 | PPI | VERNAM | 5.00 | | | | | | | | | | | | | 60 | 50 |
|  | 5.00 | PPI | VERNAM | 5.00 | | | | | | | | | | | | | 60 | — |
|  | 0.50 | PPI | EPTAM | 5.00 | | | | | | | | | 70 | 10 | | | | |
|  | 5.00 | PPI | EPTAM | 5.00 | | | | | | | | | 70 | 0 | | | | |
|  | 1.00 | PPI | SUTAN | 6.00 | | | | | 50 | — | | | | | | | | |
|  | 5.00 | PPI | SUTAN | 6.00 | | | | | 50 | 40 | | | | | | | | |
| 5 | 5.00 | IF | VERNAM | 1.00 | 95 | — | 75 | 50 | 70 | — | 95 | — | 50 | — | | | | |
|  | 5.00 | IF | VERNAM | 5.00 | | | | | | | | | | | 90 | — | 60 | 70 |
|  | 1.00 | IF | VERNAM | 1.00 | | | 100 | 80 | | | | | | | | | | |

TABLE IV-continued

Antidotal Effectiveness
% Injury

| Cmpd. No. | Antidote Rate | Method | Herbicide Name | Rate | Milo U | T | Wheat U | T | Cotton U | T | Rice U | T | Barley U | T | Corn U | T | Soybean U | T |
|---|---|---|---|---|---|---|---|---|---|---|---|---|---|---|---|---|---|---|
|  | 5.00 | IF | VERNAM | 1.00 |  |  | 100 | 80 |  |  |  |  |  |  |  |  |  |  |
|  | 1.00 | IF | VERNAM | 5.00 |  |  |  |  |  |  |  |  |  |  | 40 | — |  |  |
|  | 5.00 | IF | VERNAM | 5.00 |  |  |  |  |  |  |  |  |  |  | 40 | 60 |  |  |
|  | 0.50 | PPI | VERNAM | 6.00 |  |  |  |  |  |  |  |  |  |  | 60 | 20 |  |  |
|  | 1.00 | PPI | VERNAM | 6.00 |  |  |  |  |  |  |  |  |  |  | 60 | 45 |  |  |
|  | 0.50 | PPI | VERNAM | 7.00 |  |  |  |  |  |  |  |  |  |  | 65 | — |  |  |
|  | 1.00 | PPI | VERNAM | 7.00 |  |  |  |  |  |  |  |  |  |  | 65 | — |  |  |
|  | 2.00 | PPI | VERNAM | 7.00 |  |  |  |  |  |  |  |  |  |  | 65 | — |  |  |
| 6 | 5.00 | IF | VERNAM | 1.00 | 100 | 40 | 95 | — | 60 | — | 95 | — | 90 | — |  |  |  |  |
|  | 5.00 | IF | VERNAM | 6.00 |  |  |  |  |  |  |  |  |  |  | 90 | 0 | 50 | 90 |
|  | 1.00 | IF | RO-NEET | 3.00 | 75 | 40 |  |  |  |  |  |  |  |  |  |  |  |  |
|  | 5.00 | IF | RO-NEET | 3.00 | 75 | 20 |  |  |  |  |  |  |  |  |  |  |  |  |
| 7 | 5.00 | IF | VERNAM | 1.25 | 100 | 30 | 95 | — | 50 | — | 95 | — | 70 | 40 |  |  |  |  |
|  | 5.00 | IF | VERNAM | 6.00 |  |  |  |  |  |  |  |  |  |  | 95 | 0 | 50 | 20 |
|  | 1.00 | IF | VERNAM | 6.00 |  |  |  |  |  |  |  |  |  |  |  |  | 65 | — |
|  | 5.00 | IF | VERNAM | 6.00 |  |  |  |  |  |  |  |  |  |  |  |  | 65 | — |
|  | 1.00 | IF | RO-NEET | 3.00 | 75 | 50 |  |  |  |  |  |  |  |  |  |  |  |  |
|  | 5.00 | IF | RO-NEET | 3.00 | 75 | 50 |  |  |  |  |  |  |  |  |  |  |  |  |
| 8 | 5.00 | IF | VERNAM | 1.25 | 100 | — | 95 | 70 | 50 | — | 95 | — | 70 | — |  |  |  |  |
|  | 5.00 | IF | VERNAM | 6.00 |  |  |  |  |  |  |  |  |  |  | 95 | 60 | 50 | 90 |
|  | 1.00 | PPI | VERNAM | 6.00 |  |  |  |  |  |  |  |  |  |  |  |  | 65 | — |
|  | 2.50 | PPI | VERNAM | 6.00 |  |  |  |  |  |  |  |  |  |  |  |  | 65 | — |
|  | 5.00 | PPI | VERNAM | 6.00 |  |  |  |  |  |  |  |  |  |  |  |  | 65 | — |
|  | 1.00 | PPI | VERNAM | 6.00 |  |  |  |  |  |  |  |  |  |  |  |  | 65 | 30 |
|  | 5.00 | PPI | VERNAM | 6.00 |  |  |  |  |  |  |  |  |  |  |  |  | 65 | — |
| 9 | 5.00 | IF | VERNAM | 1.00 | 100 | — | 90 | — | 55 | — | 95 | — | 90 | — |  |  |  |  |
|  | 5.00 | IF | VERNAM | 6.00 |  |  |  |  |  |  |  |  |  |  | 70 | — | 30 | 100 |
|  | 1.00 | PPI | VERNAM | 6.00 |  |  |  |  |  |  |  |  |  |  |  |  | 60 | 35 |
|  | 5.00 | PPI | VERNAM | 6.00 |  |  |  |  |  |  |  |  |  |  |  |  | 60 | — |
| 10 | 5.00 | IF | VERNAM | 1.00 | 100 | — | 75 | — | 70 | 90 | 95 | 70 | 70 | 50 |  |  |  |  |
|  | 5.00 | IF | VERNAM | 6.00 |  |  |  |  |  |  |  |  |  |  | 90 | 30 | 80 | 70 |
|  | 1.00 | IF | VERNAM | 1.25 |  |  |  |  |  |  |  |  | 70 | — |  |  |  |  |
|  | 5.00 | IF | VERNAM | 1.25 |  |  |  |  |  |  |  |  | 70 | 60 |  |  |  |  |
|  | 0.50 | PPI | EPTAM | 5.00 |  |  |  |  |  |  |  |  |  |  | 80 | — |  |  |
|  | 5.00 | PPI | EPTAM | 5.00 |  |  |  |  |  |  |  |  |  |  | 80 | 60 |  |  |
|  | 1.00 | PPI | SUTAN | 5.00 |  |  |  |  | 35 | 50 |  |  |  |  |  |  |  |  |
|  | 5.00 | PPI | SUTAN | 5.00 |  |  |  |  | 35 | 65 |  |  |  |  |  |  |  |  |
| 11 | 5.00 | IF | VERNAM | 1.00 | 100 | — | 85 | — | 50 | — | 95 | — | 55 | — |  |  |  |  |
|  | 5.00 | IF | VERNAM | 6.00 |  |  |  |  |  |  |  |  |  |  | 80 | 95 | 60 | 80 |
|  | 1.00 | PPI | VERNAM | 6.00 |  |  |  |  |  |  |  |  |  |  |  |  | 60 | 20 |
|  | 5.00 | PPI | VERNAM | 6.00 |  |  |  |  |  |  |  |  |  |  |  |  | 60 | 70 |
| 12 | 5.00 | IF | VERNAM | 1.00 | 80 | 60 | 80 | 50 | 70 | — | 95 | 40 | 70 | 10 |  |  |  |  |
|  | 5.00 | IF | VERNAM | 6.00 |  |  |  |  |  |  |  |  |  |  | 90 | 0 | 50 | 70 |
|  | 1.00 | IF | VERNAM | 1.00 |  |  |  |  |  |  | 100 | — |  |  |  |  |  |  |
|  | 5.00 | IF | VERNAM | 1.00 |  |  |  |  |  |  | 100 | — |  |  |  |  |  |  |
|  | 1.00 | IF | VERNAM | 1.25 |  |  |  |  |  |  |  |  | 95 | — |  |  |  |  |
|  | 5.00 | IF | VERNAM | 1.25 |  |  |  |  |  |  |  |  | 95 | 40 |  |  |  |  |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | — |
|  | 0.50 | PPI | EPTAM | 5.00 |  |  |  |  |  |  |  |  |  |  | 80 | 40 |  |  |
|  | 5.00 | PPI | EPTAM | 5.00 |  |  |  |  |  |  |  |  |  |  | 80 | 0 |  |  |
| 13 | 5.00 | IF | VERNAM | 1.00 | 100 | 40 | 90 | — | 55 | 90 | 95 | 70 | 90 | 40 |  |  |  |  |
|  | 5.00 | IF | VERNAM | 6.00 |  |  |  |  |  |  |  |  |  |  | 90 | 10 | 30 | 50 |
|  | 1.00 | IF | VERNAM | 1.00 | 95 | — |  |  |  |  |  |  |  |  |  |  |  |  |
|  | 5.00 | IF | VERNAM | 1.00 | 95 | 60 |  |  |  |  |  |  |  |  |  |  |  |  |
|  | 1.00 | IF | VERNAM | 1.00 |  |  |  |  |  |  |  |  | 60 | 50 |  |  |  |  |
|  | 5.00 | IF | VERNAM | 1.00 |  |  |  |  |  |  |  |  | 60 | 40 |  |  |  |  |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | — |
|  | 0.50 | PPI | EPTAM | 5.00 |  |  |  |  |  |  |  |  |  |  | 80 | 0 |  |  |
|  | 5.00 | PPI | EPTAM | 5.00 |  |  |  |  |  |  |  |  |  |  | 80 | 0 |  |  |
|  | 1.00 | PPI | SUTAN | 5.00 |  |  |  |  | 35 | — |  |  |  |  |  |  |  |  |
|  | 5.00 | PPI | SUTAN | 5.00 |  |  |  |  | 35 | 20 |  |  |  |  |  |  |  |  |
|  | 1.00 | IF | RO-NEET | 3.00 | 75 | 40 |  |  |  |  |  |  |  |  |  |  |  |  |
|  | 5.00 | IF | RO-NEET | 3.00 | 75 | 50 |  |  |  |  |  |  |  |  |  |  |  |  |
| 14 | 5.00 | IF | VERNAM | 1.00 | 100 | 80 | 75 | 20 | 70 | 100 | 95 | 60 | 70 | 40 |  |  |  |  |
|  | 5.00 | IF | VERNAM | 6.00 |  |  |  |  |  |  |  |  |  |  |  |  | 80 | — |
|  | 1.00 | IF | VERNAM | 1.25 |  |  | 95 | — |  |  | 95 | — | 80 | — |  |  |  |  |
|  | 5.00 | IF | VERNAM | 1.25 |  |  | 95 | — |  |  | 95 | — | 80 | 50 |  |  |  |  |
|  | 5.00 | IF | VERNAM | 6.00 |  |  |  |  |  |  |  |  |  |  | 90 | 20 |  |  |
|  | 0.50 | PPI | EPTAM | 5.00 |  |  |  |  |  |  |  |  |  |  | 80 | 0 |  |  |
|  | 5.00 | PPI | EPTAM | 5.00 |  |  |  |  |  |  |  |  |  |  | 80 | 0 |  |  |
|  | 1.00 | PPI | SUTAN | 5.00 |  |  |  |  | 35 | 10 |  |  |  |  |  |  |  |  |
|  | 5.00 | PPI | SUTAN | 5.00 |  |  |  |  | 35 | — |  |  |  |  |  |  |  |  |
| 15 | 5.00 | IF | VERNAM | 1.00 | 100 | — | 85 | 50 | 50 | 30 | 95 | 10 | 55 | 30 |  |  |  |  |
|  | 5.00 | IF | VERNAM | 6.00 |  |  |  |  |  |  |  |  |  |  | 95 | 0 | 60 | 80 |
|  | 1.00 | PPI | VERNAM | 1.25 |  |  |  |  |  |  | 90 | — |  |  |  |  |  |  |

TABLE IV-continued

Antidotal Effectiveness

| Antidote | | | Herbicide | | % Injury | | | | | | | | | | | | |
|---|---|---|---|---|---|---|---|---|---|---|---|---|---|---|---|---|---|
| Cmpd. No. | Rate | Method | Name | Rate | Milo U | Milo T | Wheat U | Wheat T | Cotton U | Cotton T | Rice U | Rice T | Barley U | Barley T | Corn U | Corn T | Soybean U | Soybean T |
| | 2.00 | PPI | VERNAM | 1.25 | | | | | | | | | 90 | 60 | | | | |
| | 5.00 | PPI | VERNAM | 1.25 | | | | | | | | | 90 | 50 | | | | |
| | 1.00 | IF | VERNAM | 1.70 | | | | | | | | | 75 | 20 | | | | |
| | 5.00 | IF | VERNAM | 1.70 | | | | | | | | | 75 | 20 | | | | |
| | 1.00 | IF | VERNAM | 5.00 | | | | | | | | | | | | | 60 | — |
| | 5.00 | IF | VERNAM | 5.00 | | | | | | | | | | | | | 60 | 45 |
| | 0.50 | PPI | EPTAM | 5.00 | | | | | | | | | | | 80 | 0 | | |
| | 5.00 | PPI | EPTAM | 5.00 | | | | | | | | | | | 80 | 0 | | |
| 16 | 5.00 | IF | VERNAM | 1.00 | 80 | — | 80 | 40 | 70 | — | 95 | 30 | 70 | — | | | | |
| | 5.00 | IF | VERNAM | 6.00 | | | | | | | | | | | 90 | — | 50 | 70 |
| | 1.00 | IF | VERNAM | 1.00 | | | 100 | — | | | 100 | — | | | | | | |
| | 5.00 | IF | VERNAM | 1.00 | | | 100 | — | | | 100 | — | | | | | | |
| | 1.00 | PPI | VERNAM | 6.00 | | | | | | | | | | | | | 60 | 20 |
| | 5.00 | PPI | VERNAM | 6.00 | | | | | | | | | | | | | 60 | — |
| 17 | 5.00 | IF | VERNAM | 1.00 | 95 | — | 90 | 40 | 50 | — | 100 | — | 60 | — | | | | |
| | 5.00 | IF | VERNAM | 6.00 | | | | | | | | | | | 95 | — | 50 | — |
| | 1.00 | IF | VERNAM | 1.00 | | | 100 | — | | | | | | | | | | |
| | 5.00 | IF | VERNAM | 1.00 | | | 100 | — | | | | | | | | | | |
| 18 | 5.00 | IF | VERNAM | 1.00 | 100 | — | 95 | — | 60 | — | 95 | — | 95 | 60 | | | | |
| | 5.00 | IF | VERNAM | 6.00 | | | | | | | | | | | 85 | 0 | 60 | — |
| 19 | 5.00 | IF | VERNAM | 1.25 | 100 | — | 85 | — | 60 | — | 100 | — | 80 | — | | | | |
| | 5.00 | IF | VERNAM | 6.00 | | | | | | | | | | | 90 | 30 | 60 | 80 |
| | 1.00 | PPI | VERNAM | 5.00 | | | | | | | | | | | | | 60 | — |
| | 5.00 | PPI | VERNAM | 5.00 | | | | | | | | | | | | | 60 | — |
| | 0.50 | PPI | EPTAM | 5.00 | | | | | | | | | | | 70 | 50 | | |
| | 5.00 | PPI | EPTAM | 5.00 | | | | | | | | | | | 70 | 40 | | |
| 20 | 5.00 | IF | VERNAM | 1.25 | 100 | — | 95 | — | 60 | 40 | 100 | 60 | 90 | 70 | | | | |
| | 5.00 | IF | VERNAM | 6.00 | | | | | | | | | | | 85 | 20 | 70 | 80 |
| | 0.50 | PPI | VERNAM | 6.00 | | | | | | | | | | | | | 60 | 85 |
| | 2.00 | PPI | VERNAM | 6.00 | | | | | | | | | | | | | 60 | 95 |
| | 0.50 | PPI | VERNAM | 6.00 | | | | | | | | | | | | | 55 | 85 |
| | 2.00 | PPI | VERNAM | 6.00 | | | | | | | | | | | | | 55 | 90 |
| | 0.50 | PPI | EPTAM | 5.00 | | | | | | | | | | | 70 | 10 | | |
| | 5.00 | PPI | EPTAM | 5.00 | | | | | | | | | | | 70 | 0 | | |
| | 1.00 | IF | SUTAN | 5.00 | | | | | 60 | 50 | | | | | | | | |
| | 5.00 | IF | SUTAN | 5.00 | | | | | 60 | 50 | | | | | | | | |
| 21 | 5.00 | IF | VERNAM | 1.25 | 100 | 40 | 95 | — | 60 | — | 100 | — | 95 | 70 | | | | |
| | 5.00 | IF | VERNAM | 6.00 | | | | | | | | | | | 85 | 0 | 70 | — |
| | 0.50 | PPI | EPTAM | 5.00 | | | | | | | | | | | 70 | 0 | | |
| | 5.00 | PPI | EPTAM | 5.00 | | | | | | | | | | | 70 | 0 | | |
| | 1/20 | PPI | EPTAM | 6.00 | | | | | | | | | | | 90 | 50 | | |
| | 1/40 | PPI | EPTAM | 6.00 | | | | | | | | | | | 90 | 70 | | |
| | 1/400 | PPI | EPTAM | 6.00 | | | | | | | | | | | 90 | — | | |
| | 1.00 | IF | RO-NEET | 3.00 | 65 | 30 | | | | | | | | | | | | |
| | 5.00 | IF | RO-NEET | 3.00 | 65 | 20 | | | | | | | | | | | | |
| 22 | 5.00 | IF | VERNAM | 1.25 | 80 | 40 | 85 | — | 60 | — | 65 | 10 | 55 | 0 | | | | |
| | 5.00 | IF | VERNAM | 6.00 | | | | | | | | | | | 90 | 75 | 70 | 100 |
| | 1.00 | PPI | VERNAM | 1.00 | | | | | | | 90 | 80 | | | | | | |
| | 5.00 | PPI | VERNAM | 1.00 | | | | | | | 90 | 80 | | | | | | |
| | 1.00 | IF | VERNAM | 1.25 | | | | | | | 99 | — | | | | | | |
| | 5.00 | IF | VERNAM | 1.25 | | | | | | | 99 | — | | | | | | |
| | 1.00 | IF | VERNAM | 1.25 | | | | | | | | | 90 | — | | | | |
| | 5.00 | IF | VERNAM | 1.25 | | | | | | | | | 90 | — | | | | |
| | 1.00 | IF | VERNAM | 1.25 | | | | | | | | | 85 | — | | | | |
| | 5.00 | IF | VERNAM | 1.25 | | | | | | | | | 85 | 75 | | | | |
| | 1.00 | IF | RO-NEET | 3.00 | 95 | — | | | | | | | | | | | | |
| | 5.00 | IF | RO-NEET | 3.00 | 95 | — | | | | | | | | | | | | |
| 23 | 5.00 | IF | VERNAM | 1.00 | 100 | — | 85 | 60 | 50 | 40 | 95 | — | 55 | — | | | | |
| | 5.00 | IF | VERNAM | 6.00 | | | | | | | | | | | 95 | 80 | 60 | 20 |
| | 1.00 | IF | VERNAM | 6.00 | | | | | | | | | | | | | 50 | 70 |
| | 5.00 | IF | VERNAM | 6.00 | | | | | | | | | | | | | 50 | 70 |
| | 0.50 | PPI | VERNAM | 7.00 | | | | | | | | | | | | | 50 | 20 |
| | 1.00 | PPI | VERNAM | 7.00 | | | | | | | | | | | | | 50 | 30 |
| | 2.00 | PPI | VERNAM | 7.00 | | | | | | | | | | | | | 50 | — |
| | 0.50 | PPI | VERNAM | 7.00 | | | | | | | | | | | | | 65 | 50 |
| | 1.00 | PPI | VERNAM | 7.00 | | | | | | | | | | | | | 65 | — |
| | 2.00 | PPI | VERNAM | 7.00 | | | | | | | | | | | | | 65 | — |
| 24 | 5.00 | IF | VERNAM | 1.25 | 100 | 70 | 95 | — | 50 | — | 95 | — | 70 | — | | | | |
| | 5.00 | IF | VERNAM | 6.00 | | | | | | | | | | | 95 | 70 | 50 | 70 |
| | 1.00 | PPI | VERNAM | 6.00 | | | | | | | | | | | | | 65 | — |
| | 2.50 | PPI | VERNAM | 6.00 | | | | | | | | | | | | | 65 | — |
| | 5.00 | PPI | VERNAM | 6.00 | | | | | | | | | | | | | 65 | — |
| | 1.00 | PPI | VERNAM | 6.00 | | | | | | | | | | | | | 60 | — |
| | 5.00 | PPI | VERNAM | 6.00 | | | | | | | | | | | | | 60 | — |
| 25 | 5.00 | IF | VERNAM | 1.00 | 100 | — | 85 | 60 | 50 | — | 95 | — | 55 | — | | | | |
| | 5.00 | IF | VERNAM | 6.00 | | | | | | | | | | | 95 | — | 60 | 90 |
| | 1.00 | PPI | VERNAM | 6.00 | | | | | | | | | | | | | 60 | 40 |

TABLE IV-continued

Antidotal Effectiveness

| Antidote | | | Herbicide | | % Injury | | | | | | | | | | | | |
|---|---|---|---|---|---|---|---|---|---|---|---|---|---|---|---|---|---|
| Cmpd. | | | | | Milo | | Wheat | | Cotton | | Rice | | Barley | | Corn | | Soybean | |
| No. | Rate | Method | Name | Rate | U | T | U | T | U | T | U | T | U | T | U | T | U | T |
|  | 5.00 | PPI | VERNAM | 6.00 |  |  |  |  |  |  |  |  |  |  |  |  | 60 | 80 |
| 26 | 5.00 | IF | VERNAM | 1.00 | 100 | 70 | 85 | 60 | 50 | — | 95 | — | 55 | — |  |  |  |  |
|  | 5.00 | IF | VERNAM | 6.00 |  |  |  |  |  |  |  |  |  |  | 95 | 20 | 60 | 90 |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | 75 |
|  | 0.50 | PPI | EPTAM | 5.00 |  |  |  |  |  |  |  |  |  |  | 80 | 0 |  |  |
|  | 5.00 | PPI | EPTAM | 5.00 |  |  |  |  |  |  |  |  |  |  | 80 | 0 |  |  |
| 27 | 5.00 | IF | VERNAM | 1.25 | 100 | — | 100 | 80 | 50 | — | 100 | 80 | 90 | 30 |  |  |  |  |
|  | 5.00 | IF | VERNAM | 6.00 |  |  |  |  |  |  |  |  |  |  | 90 | 10 | 70 | — |
|  | 0.50 | PPI | EPTAM | 5.00 |  |  |  |  |  |  |  |  |  |  | 70 | 0 |  |  |
|  | 5.00 | PPI | EPTAM | 5.00 |  |  |  |  |  |  |  |  |  |  | 70 | 0 |  |  |
| 28 | 5.00 | IF | VERNAM | 1.00 | 100 | — | 85 | 100 | 50 | 80 | 95 | 100 | 55 | 95 |  |  |  |  |
|  | 5.00 | IF | VERNAM | 6.00 |  |  |  |  |  |  |  |  |  |  | 95 | — | 60 | 80 |
|  | 1.00 | PPI | VERNAM | 1.25 |  |  |  |  |  |  |  |  | 70 | 100 |  |  |  |  |
|  | 5.00 | PPI | VERNAM | 1.25 |  |  |  |  |  |  |  |  | 70 | 100 |  |  |  |  |
|  | 1.00 | PPI | VERNAM | 1.00 |  |  |  |  |  |  | 95 | — |  |  |  |  |  |  |
|  | 5.00 | PPI | VERNAM | 1.00 |  |  |  |  |  |  | 95 | — |  |  |  |  |  |  |
|  | 0.25 | PPI | VERNAM | 1.25 |  |  |  |  |  |  |  |  | 90 | — |  |  |  |  |
|  | 0.50 | PPI | VERNAM | 1.25 |  |  |  |  |  |  |  |  | 90 | — |  |  |  |  |
|  | 1.00 | PPI | VERNAM | 1.25 |  |  |  |  |  |  |  |  | 90 | — |  |  |  |  |
|  | 1.00 | PPI | VERNAM | 6.00 |  |  |  |  |  |  |  |  |  |  |  |  | 60 | 70 |
|  | 5.00 | PPI | VERNAM | 6.00 |  |  |  |  |  |  |  |  |  |  |  |  | 60 | 70 |
|  | 1.00 | IF | RO-NEET | 4.00 | 60 | — |  |  |  |  |  |  |  |  |  |  |  |  |
|  | 5.00 | IF | RO-NEET | 4.00 | 60 | 90 |  |  |  |  |  |  |  |  |  |  |  |  |
|  | 1.00 | PPI | RO-NEET | 3.00 | 95 | — |  |  |  |  |  |  |  |  |  |  |  |  |
|  | 5.00 | PPI | RO-NEET | 3.00 | 95 | — |  |  |  |  |  |  |  |  |  |  |  |  |
|  | 1.00 | PPI | SUTAN | 5.00 |  |  |  |  | 35 | 40 |  |  |  |  |  |  |  |  |
|  | 5000 | PPI | SUTAN | 5.00 |  |  |  |  | 35 | 40 |  |  |  |  |  |  |  |  |
| 29 | 5.00 | IF | VERNAM | 1.00 | 100 | — | 85 | 30 | 50 | 70 | 95 | — | 55 | 30 |  |  |  |  |
|  | 5.00 | IF | VERNAM | 5.00 |  |  |  |  |  |  |  |  |  |  | 95 | — | 60 | 100 |
|  | 1.00 | IF | VERNAM | 1.00 |  |  | 100 | — |  |  |  |  |  |  |  |  |  |  |
|  | 5.00 | IF | VERNAM | 1.00 |  |  | 100 | 60 |  |  |  |  |  |  |  |  |  |  |
|  | 1.00 | IF | VERNAM | 1.70 |  |  |  |  |  |  |  |  | 75 | 50 |  |  |  |  |
|  | 5.00 | IF | VERNAM | 1.70 |  |  |  |  |  |  |  |  | 75 | 30 |  |  |  |  |
|  | 1.00 | PPI | VERNAM | 1.25 |  |  |  |  |  |  |  |  | 70 | — |  |  |  |  |
|  | 5.00 | PPI | VERNAM | 1.25 |  |  |  |  |  |  |  |  | 70 | 60 |  |  |  |  |
|  | 1.00 | PPI | VERNAM | 6.00 |  |  |  |  |  |  |  |  |  |  |  |  | 60 | 10 |
|  | 5.00 | PPI | VERNAM | 6.00 |  |  |  |  |  |  |  |  |  |  |  |  | 60 | — |
|  | 5.00 | PFS | LASSO | 3.00 | 90 | — | 55 | — |  |  |  |  |  |  |  |  |  |  |
|  | 5.00 | PES | LASSO | 4.00 |  |  |  |  |  |  |  |  | 80 | 70 |  |  |  |  |
| 30 | 5.00 | IF | VERNAM | 1.25 | 100 | 40 | 95 | 50 | 60 | 30 | 100 | 50 | 90 | 70 |  |  |  |  |
|  | 5.00 | IF | VERNAM | 6.00 |  |  |  |  |  |  |  |  |  |  | 85 | 0 | 70 | — |
|  | 1.00 | IF | VERNAM | 1.00 |  |  | 70 | — |  |  |  |  |  |  |  |  |  |  |
|  | 5.00 | IF | VERNAM | 1.00 |  |  | 70 | — |  |  |  |  |  |  |  |  |  |  |
|  | 1.00 | IF | VERNAM | 1.25 |  |  |  |  |  |  |  |  | 85 | 80 |  |  |  |  |
|  | 5.00 | IF | VERNAM | 1.25 |  |  |  |  |  |  |  |  | 85 | 25 |  |  |  |  |
|  | 0.50 | PPI | VERNAM | 1.25 |  |  |  |  |  |  |  |  | 85 | — |  |  |  |  |
|  | 1.00 | PPI | VERNAM | 1.25 |  |  |  |  |  |  |  |  | 85 | — |  |  |  |  |
|  | 2.00 | PPI | VERNAM | 1.25 |  |  |  |  |  |  |  |  | 85 | — |  |  |  |  |
|  | 1.00 | PPI | EPTAM | 5.00 |  |  |  |  |  |  |  |  |  |  | 70 | 40 |  |  |
|  | 5.00 | PPI | EPTAM | 5.00 |  |  |  |  |  |  |  |  |  |  | 70 | 0 |  |  |
|  | 1.00 | IF | SUTAN | 5.00 |  |  |  |  | 60 | 55 |  |  |  |  |  |  |  |  |
|  | 5.00 | IF | SUTAN | 5.00 |  |  |  |  | 60 | 30 |  |  |  |  |  |  |  |  |
|  | 1.00 | PPI | SUTAN | 6.00 |  |  |  |  | 60 | 30 |  |  |  |  |  |  |  |  |
|  | 5.00 | PPI | SUTAN | 6.00 |  |  |  |  | 60 | — |  |  |  |  |  |  |  |  |
|  | 0.50 | PPI | SUTAN | 6.00 |  |  |  |  | 45 | — |  |  |  |  |  |  |  |  |
|  | 1.00 | PPI | SUTAN | 6.00 |  |  |  |  | 45 | — |  |  |  |  |  |  |  |  |
|  | 2.00 | PPI | SUTAN | 6.00 |  |  |  |  | 45 | 35 |  |  |  |  |  |  |  |  |
| 31 | 5.00 | IF | VERNAM | 1.00 | 95 | — | 90 | 50 | 50 | 70 | 100 | — | 60 | — |  |  |  |  |
|  | 5.00 | IF | VERNAM | 6.00 |  |  |  |  |  |  |  |  |  |  | 95 | — | 50 | 80 |
|  | 1.00 | IF | VERNAM | 1.00 |  |  | 100 | — |  |  |  |  |  |  |  |  |  |  |
|  | 5.00 | IF | VERNAM | 1.00 |  |  | 100 | — |  |  |  |  |  |  |  |  |  |  |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | 75 |
|  | 1.00 | PPI | SUTAN | 5.00 |  |  |  |  | 35 | — |  |  |  |  |  |  |  |  |
|  | 5.00 | PPI | SUTAN | 5.00 |  |  |  |  | 35 | — |  |  |  |  |  |  |  |  |
| 32 | 0.50 | IF | VERNAM | 1.00 | 95 | 80 | 90 | — | 50 | — | 100 | — | 60 | 40 |  |  |  |  |
|  | 5.00 | IF | VERNAM | 6.00 |  |  |  |  |  |  |  |  |  |  | 95 | 0 | 50 | — |
|  | 0.50 | PPI | EPTAM | 5.00 |  |  |  |  |  |  |  |  |  |  | 80 | 20 |  |  |
|  | 5.00 | PPI | EPTAM | 5.00 |  |  |  |  |  |  |  |  |  |  | 80 | 0 |  |  |
| 33 | 5.00 | IF | VERNAM | 1.00 | 95 | — | 90 | — | 50 | 20 | 100 | — | 60 | 30 |  |  |  |  |
|  | 5.00 | IF | VERNAM | 6.00 |  |  |  |  |  |  |  |  |  |  | 95 | 75 | 50 | — |
|  | 1.00 | IF | VERNAM | 1.25 |  |  |  |  |  |  |  |  | 100 | — |  |  |  |  |
|  | 5.00 | IF | VERNAM | 1.25 |  |  |  |  |  |  |  |  | 100 | — |  |  |  |  |
| 34 | 5.00 | IF | VERNAM | 1.00 | 95 | 100 | 90 | 100 | 50 | — | 100 | — | 60 | 100 |  |  |  |  |
|  | 5.00 | IF | VERNAM | 6.00 |  |  |  |  |  |  |  |  |  |  | 95 | — | 50 | — |
|  | 1.00 | PPI | VERNAM | 1.00 |  |  |  |  |  |  | 95 | — |  |  |  |  |  |  |

TABLE IV-continued

Antidotal Effectiveness

| Antidote | | | Herbicide | | % Injury | | | | | | | | | | | | | |
|---|---|---|---|---|---|---|---|---|---|---|---|---|---|---|---|---|---|---|
| | | | | | Milo | | Wheat | | Cotton | | Rice | | Barley | | Corn | | Soybean | |
| Cmpd. No. | Rate | Method | Name | Rate | U | T | U | T | U | T | U | T | U | T | U | T | U | T |
| | 5.00 | PPI | VERNAM | 1.00 | | | | | | | 95 | — | | | | | | |
| | 1.00 | PPI | VERNAM | 1.25 | | | | | | | | | 70 | 100 | | | | |
| | 5.00 | PPI | VERNAM | 1.25 | | | | | | | | | 70 | 100 | | | | |
| | 0.25 | PPI | VERNAM | 1.25 | | | | | | | | | 90 | — | | | | |
| | 0.50 | PPI | VERNAM | 1.25 | | | | | | | | | 90 | — | | | | |
| | 1.00 | PPI | VERNAM | 1.25 | | | | | | | | | 90 | — | | | | |
| | 1.00 | PPI | RO-NEET | 3.00 | 95 | — | | | | | | | | | | | | |
| | 5.00 | PPI | RO-NEET | 3.00 | 95 | — | | | | | | | | | | | | |
| 35 | 5.00 | IF | VERNAM | 1.25 | 90 | 80 | 100 | — | 70 | — | 100 | — | 75 | — | | | | |
| | 5.00 | IF | VERNAM | 1.25 | | | | | | | | | | | 90 | 30 | 40 | — |
| 36 | 5.00 | IF | VERNAM | 1.00 | 95 | — | 90 | — | 50 | 20 | 100 | — | 60 | 30 | | | | |
| | 5.00 | IF | VERNAM | 6.00 | | | | | | | | | | | 95 | — | 50 | 30 |
| | 1.00 | IF | VERNAM | 1.25 | | | | | | | | | 100 | — | | | | |
| | 5.00 | IF | VERNAM | 1.25 | | | | | | | | | 100 | 60 | | | | |
| | 1.00 | IF | VERNAM | 6.00 | | | | | | | | | | | | | 40 | 30 |
| | 5.00 | IF | VERNAM | 6.00 | | | | | | | | | | | | | 40 | 60 |
| | 0.50 | PPI | VERNAM | 7.00 | | | | | | | | | | | | | 50 | — |
| | 1.00 | PPI | VERNAM | 7.00 | | | | | | | | | | | | | 50 | 40 |
| | 2.00 | PPI | VERNAM | 7.00 | | | | | | | | | | | | | 50 | — |
| 37 | 5.00 | IF | VERNAM | 1.25 | 90 | — | 100 | — | 70 | 100 | 100 | — | 75 | — | | | | |
| | 5.00 | IF | VERNAM | 6.00 | | | | | | | | | | | 90 | 30 | 40 | — |
| 38 | 5.00 | IF | VERNAM | 1.25 | 100 | 60 | 95 | — | 60 | — | 100 | — | 90 | 50 | | | | |
| | 5.00 | IF | VERNAM | 6.00 | | | | | | | | | | | 85 | — | 70 | 90 |
| | 0.50 | PPI | VERNAM | 6.00 | | | | | | | | | | | | | 60 | — |
| | 2.00 | PPI | VERNAM | 6.00 | | | | | | | | | | | | | 60 | 80 |
| | 0.50 | PPI | VERNAM | 6.00 | | | | | | | | | | | | | 55 | — |
| | 2.00 | PPI | VERNAM | 6.00 | | | | | | | | | | | | | 55 | — |
| 39 | 5.00 | IF | VERNAM | 1.25 | 100 | 70 | 95 | — | 60 | — | 100 | — | 90 | — | | | | |
| | 5.00 | IF | VERNAM | 6.00 | | | | | | | | | | | 85 | — | 70 | 80 |
| | 0.50 | PPI | VERNAM | 6.00 | | | | | | | | | | | | | 55 | 85 |
| | 2.00 | PPI | VERNAM | 6.00 | | | | | | | | | | | | | 55 | 90 |
| 40 | 5.00 | IF | VERNAM | 1.25 | 100 | 60 | 95 | — | 60 | — | 100 | — | 90 | — | | | | |
| | 5.00 | IF | VERNAM | 6.00 | | | | | | | | | | | 85 | 30 | 70 | 80 |
| | 0.50 | PPI | VERNAM | 6.00 | | | | | | | | | | | | | 60 | — |
| | 2.00 | PPI | VERNAM | 6.00 | | | | | | | | | | | | | 60 | — |
| | 0.50 | PPI | VERNAM | 6.00 | | | | | | | | | | | | | 55 | — |
| | 2.00 | PPI | VERNAM | 6.00 | | | | | | | | | | | | | 55 | — |
| | 0.50 | PPI | EPTAM | 5.00 | | | | | | | | | 70 | — | | | | |
| | 5.00 | PPI | EPTAM | 5.00 | | | | | | | | | 70 | 30 | | | | |
| 41 | 5.00 | IF | VERNAM | 1.25 | 100 | — | 95 | — | 60 | — | 100 | — | 90 | — | | | | |
| | 5.00 | IF | VERNAM | 6.00 | | | | | | | | | | | 85 | 60 | 70 | 80 |
| 42 | 5.00 | IF | VERNAM | 1.25 | 100 | — | 100 | 80 | 50 | — | 100 | — | 90 | 70 | | | | |
| | 5.00 | IF | VERNAM | 6.00 | | | | | | | | | | | 90 | — | 70 | 50 |
| 43 | 5.00 | IF | VERNAM | 1.25 | 100 | — | 85 | — | 60 | — | 100 | — | 80 | — | | | | |
| | 5.00 | IF | VERNAM | 6.00 | | | | | | | | | | | 90 | 60 | 60 | 100 |
| | 1.00 | PPI | VERNAM | 5.00 | | | | | | | | | | | | | 60 | 50 |
| | 5.00 | PPI | VERNAM | 5.00 | | | | | | | | | | | | | 60 | — |
| 44 | 5.00 | IF | VERNAM | 1.00 | 85 | 50 | 70 | — | 50 | 40 | 70 | — | 55 | — | | | | |
| | 5.00 | IF | VERNAM | 6.00 | | | | | | | | | | | 90 | 10 | 55 | 10 |
| | 1.00 | IF | VERNAM | 5.00 | | | | | | | | | | | | | 60 | — |
| | 5.00 | IF | VERNAM | 5.00 | | | | | | | | | | | | | 60 | — |
| | 0.50 | PPI | EPTAM | 5.00 | | | | | | | | | 80 | 50 | | | | |
| | 5.00 | PPI | EPTAM | 5.00 | | | | | | | | | 80 | 20 | | | | |
| 45 | 5.00 | IF | VERNAM | 1.00 | 80 | — | 80 | — | 70 | 60 | 95 | 40 | 70 | 30 | | | | |
| | 5.00 | IF | VERNAM | 6.00 | | | | | | | | | | | 90 | — | 50 | — |
| | 1.00 | IF | VERNAM | 1.00 | | | | | | | 100 | — | | | | | | |
| | 5.00 | IF | VERNAM | 1.00 | | | | | | | 100 | — | | | | | | |
| | 1.00 | IF | VERNAM | 1.25 | | | | | | | | | 95 | — | | | | |
| | 5.00 | IF | VERNAM | 1.25 | | | | | | | | | 95 | — | | | | |
| 46 | 5.00 | IF | VERNAM | 1.25 | 80 | 75 | 85 | 40 | 60 | 55 | 65 | 45 | 55 | 20 | | | | |
| | 5.00 | IF | VERNAM | 6.00 | | | | | | | | | | | 90 | 80 | 70 | 40 |
| | 1.00 | IF | VERNAM | 1.00 | | | 95 | — | | | | | | | | | | |
| | 5.00 | IF | VERNAM | 1.00 | | | 95 | 80 | | | | | | | | | | |
| | 1.00 | IF | VERNAM | 1.25 | | | | | | | | | 90 | 80 | | | | |
| | 5.00 | IF | VERNAM | 1.25 | | | | | | | | | 90 | — | | | | |
| 47 | 5.00 | IF | VERNAM | 1.00 | 100 | — | 85 | 50 | 50 | — | 95 | — | 55 | — | | | | |
| | 5.00 | IF | VERNAM | 6.00 | | | | | | | | | | | 95 | — | 60 | 90 |
| | 1.00 | PPI | VERNAM | 6.00 | | | | | | | | | | | | | 60 | — |
| | 5.00 | PPI | VERNAM | 6.00 | | | | | | | | | | | | | 60 | 80 |
| 48 | 5.00 | IF | VERNAM | 1.00 | 100 | 80 | 85 | 60 | 50 | 80 | 95 | — | 55 | — | | | | |
| | 5.00 | IF | VERNAM | 6.00 | | | | | | | | | | | 95 | — | 60 | 80 |
| | 1.00 | PPI | VERNAM | 6.00 | | | | | | | | | | | | | 60 | — |
| | 5.00 | PPI | VERNAM | 6.00 | | | | | | | | | | | | | 60 | 80 |
| | 1.00 | PPI | SUTAN | 5.00 | | | | | 35 | 60 | | | | | | | | |
| | 5.00 | PPI | SUTAN | 5.00 | | | | | 35 | — | | | | | | | | |
| 49 | 5.00 | IF | VERNAM | 1.00 | 100 | — | 85 | — | 50 | — | 95 | 100 | 55 | 100 | | | | |
| | 5.00 | IF | VERNAM | 6.00 | | | | | | | | | | | 95 | — | 60 | 90 |

TABLE IV-continued

Antidotal Effectiveness % Injury

| Cmpd. No. | Antidote Rate | Method | Herbicide Name | Rate | Milo U | Milo T | Wheat U | Wheat T | Cotton U | Cotton T | Rice U | Rice T | Barley U | Barley T | Corn U | Corn T | Soybean U | Soybean T |
|---|---|---|---|---|---|---|---|---|---|---|---|---|---|---|---|---|---|---|
|  | 1.00 | PPI | VERNAM | 1.00 |  |  |  |  |  |  | 95 | — |  |  |  |  |  |  |
|  | 5.00 | PPI | VERNAM | 1.00 |  |  |  |  |  |  | 95 | — |  |  |  |  |  |  |
|  | 1.00 | PPI | VERNAM | 1.25 |  |  |  |  |  |  |  |  | 70 | 100 |  |  |  |  |
|  | 5.00 | PPI | VERNAM | 1.25 |  |  |  |  |  |  |  |  | 70 | 100 |  |  |  |  |
|  | 0.25 | PPI | VERNAM | 1.25 |  |  |  |  |  |  |  |  | 90 | — |  |  |  |  |
|  | 0.50 | PPI | VERNAM | 1.25 |  |  |  |  |  |  |  |  | 90 | — |  |  |  |  |
|  | 1.00 | PPI | VERNAM | 1.25 |  |  |  |  |  |  |  |  | 90 | — |  |  |  |  |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | 85 |
|  | 1.00 | IF | RO-NEET | 4.00 | 60 | 70 |  |  |  |  |  |  |  |  |  |  |  |  |
|  | 5.00 | IF | RO-NEET | 4.00 | 60 | 100 |  |  |  |  |  |  |  |  |  |  |  |  |
|  | 1.00 | PPI | RO-NEET | 3.00 | 95 | 60 |  |  |  |  |  |  |  |  |  |  |  |  |
|  | 5.00 | PPI | RO-NEET | 3.00 | 95 | 20 |  |  |  |  |  |  |  |  |  |  |  |  |
|  | 0.25 | PPI | RO-NEET | 3.00 | 75 | — |  |  |  |  |  |  |  |  |  |  |  |  |
|  | 0.50 | PPI | RO-NEET | 3.00 | 75 | — |  |  |  |  |  |  |  |  |  |  |  |  |
|  | 1.00 | PPI | RO-NEET | 3.00 | 75 | — |  |  |  |  |  |  |  |  |  |  |  |  |
| 50 | 5.00 | IF | VERNAM | 1.00 | 100 | — | 85 | 40 | 50 | — | 95 | — | 55 | 30 |  |  |  |  |
|  | 5.00 | IF | VERNAM | 6.00 |  |  |  |  |  |  |  |  |  |  | 95 | — | 60 | 90 |
|  | 1.00 | IF | VERNAM | 1.00 |  |  | 100 | — |  |  |  |  |  |  |  |  |  |  |
|  | 5.00 | IF | VERNAM | 1.00 |  |  | 100 | 70 |  |  |  |  |  |  |  |  |  |  |
|  | 1.00 | IF | VERNAM | 1.70 |  |  |  |  |  |  |  |  | 75 | 60 |  |  |  |  |
|  | 5.00 | IF | VERNAM | 1.70 |  |  |  |  |  |  |  |  | 75 | 40 |  |  |  |  |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | 80 |
| 51 | 5.00 | IF | VERNAM | 1.00 | 100 | 60 | 85 | 60 | 50 | — | 95 | — | 55 | — |  |  |  |  |
|  | 5.00 | IF | VERNAM | 6.00 |  |  |  |  |  |  |  |  |  |  | 95 | 40 | 60 | 90 |
|  | 1.00 | PPI | VERNAM | 6.00 |  |  |  |  |  |  |  |  |  |  |  |  | 60 | — |
|  | 5.00 | PPI | VERNAM | 6.00 |  |  |  |  |  |  |  |  |  |  |  |  | 60 | 80 |
| 52 | 5.00 | IF | VERNAM | 1.00 | 100 | 80 | 85 | 40 | 50 | — | 95 | — | 55 | — |  |  |  |  |
|  | 5.00 | IF | VERNAM | 6.00 |  |  |  |  |  |  |  |  |  |  | 95 | — | 60 | 90 |
|  | 1.00 | IF | VERNAM | 1.00 |  |  | 100 | — |  |  |  |  |  |  |  |  |  |  |
|  | 5.00 | IF | VERNAM | 1.00 |  |  | 100 | 65 |  |  |  |  |  |  |  |  |  |  |
|  | 1.00 | PPI | VERNAM | 6.00 |  |  |  |  |  |  |  |  |  |  |  |  | 60 | 20 |
|  | 5.00 | PPI | VERNAM | 6.00 |  |  |  |  |  |  |  |  |  |  |  |  | 60 | — |
|  | 5.00 | PES | LASSO | 3.00 | 90 | — | 55 | — |  |  |  |  |  |  |  |  |  |  |
|  | 5.00 | PES | LASSO | 4.00 |  |  |  |  |  |  |  |  | 80 | 60 |  |  |  |  |
| 53 | 5.00 | IF | VERNAM | 1.25 | 100 | 50 | 100 | 70 | 50 | — | 100 | 70 | 90 | 50 |  |  |  |  |
|  | 5.00 | IF | VERNAM | 6.00 |  |  |  |  |  |  |  |  |  |  | 90 | 70 | 70 | 60 |
|  | 1.00 | IF | VERNAM | 5.00 |  |  |  |  |  |  |  |  |  |  |  |  | 60 | — |
|  | 5.00 | IF | VERNAM | 5.00 |  |  |  |  |  |  |  |  |  |  |  |  | 60 | 80 |
|  | 1.00 | IF | RO-NEET | 3.00 | 75 | 50 |  |  |  |  |  |  |  |  |  |  |  |  |
|  | 5.00 | IF | RO-NEET | 3.00 | 75 | 40 |  |  |  |  |  |  |  |  |  |  |  |  |
| 54 | 1.00 | IF | VERNAM | 1.00 | 100 | 60 | 95 | — | 60 | — | 95 | — | 90 | 100 |  |  |  |  |
|  | 5.00 | IF | VERNAM | 6.00 |  |  |  |  |  |  |  |  |  |  | 90 | 60 | 50 | 90 |
|  | 1.00 | PPI | VERNAM | 1.25 |  |  |  |  |  |  |  |  | 70 | — |  |  |  |  |
|  | 5.00 | PPI | VERNAM | 1.25 |  |  |  |  |  |  |  |  | 70 | — |  |  |  |  |
| 55 | 5.00 | IF | VERNAM | 1.00 | 100 | 60 | 95 | 70 | 60 | — | 95 | — | 90 | 70 |  |  |  |  |
|  | 5.00 | IF | VERNAM | 6.00 |  |  |  |  |  |  |  |  |  |  | 90 | 0 | 50 | — |
| 56 | 5.00 | IF | VERNAM | 1.00 | 100 | 50 | 95 | 70 | 60 | — | 95 | — | 90 | — |  |  |  |  |
|  | 5.00 | IF | VERNAM | 6.00 |  |  |  |  |  |  |  |  |  |  | 90 | 70 | 50 | 80 |
|  | 1.00 | IF | RO-NEET | 3.00 | 75 | 50 |  |  |  |  |  |  |  |  |  |  |  |  |
|  | 5.00 | IF | RO-NEET | 3.00 | 75 | 50 |  |  |  |  |  |  |  |  |  |  |  |  |
| 57 | 5.00 | IF | VERNAM | 1.25 | 100 | — | 100 | — | 50 | 80 | 100 | — | 90 | 100 |  |  |  |  |
|  | 5.00 | IF | VERNAM | 6.00 |  |  |  |  |  |  |  |  |  |  | 90 | 50 | 70 | 80 |
| 58 | 5.00 | IF | VERNAM | 1.00 | 100 | 40 | 95 | — | 60 | — | 95 | — | 90 | 70 |  |  |  |  |
|  | 5.00 | IF | VERNAM | 6.00 |  |  |  |  |  |  |  |  |  |  | 90 | 60 | 50 | 80 |
|  | 1.00 | IF | RO-NEET | 3.00 | 75 | — |  |  |  |  |  |  |  |  |  |  |  |  |
|  | 5.00 | IF | RO-NEET | 3.00 | 75 | — |  |  |  |  |  |  |  |  |  |  |  |  |
| 59 | 5.00 | IF | VERNAM | 1.00 | 100 | — | 95 | — | 60 | — | 95 | — | 90 | — |  |  |  |  |
|  | 5.00 | IF | VERNAM | 6.00 |  |  |  |  |  |  |  |  |  |  | 90 | — | 50 | 70 |
| 60 | 5.00 | IF | VERNAM | 1.00 | 100 | 70 | 95 | 70 | 60 | — | 95 | — | 90 | — |  |  |  |  |
|  | 5.00 | IF | VERNAM | 6.00 |  |  |  |  |  |  |  |  |  |  | 90 | — | 50 | — |

TABLE V

Herbicidal Effectiveness % Injury

| Cmpd. No. | Antidote Rate | Method | Herbicide Name | Rate | Water-grass U | Water-grass T | Foxtail U | Foxtail T | Wild Oat U | Wild Oat T | Johnson-grass U | Johnson-grass T | Shatter-cane U | Shatter-cane T | Nutsedge U | Nutsedge T |
|---|---|---|---|---|---|---|---|---|---|---|---|---|---|---|---|---|
| 1 | 1.00 | PPI | VERNAM | 6.00 | 100 | — | 100 | — |  |  |  |  |  |  |  |  |
|  | 5.00 | PPI | VERNAM | 6.00 | 100 | — | 100 | — |  |  |  |  |  |  |  |  |
|  | 1.00 | PPI | VERNAM | 6.00 | 85 | — | 90 | — |  |  |  |  |  |  |  |  |
|  | 5.00 | PPI | VERNAM | 6.00 | 85 | — | 90 | — |  |  |  |  |  |  |  |  |
|  | 0.50 | PPI | EPTAM | 5.00 | 100 | — | 100 | — |  |  |  |  |  |  |  |  |

TABLE V-continued

|   |      |     |         |      |     |    |     |    |     |    |    |    |
|---|------|-----|---------|------|-----|----|-----|----|-----|----|----|----|
|   | 5.00 | PPI | EPTAM   | 5.00 | 100 | —  | 100 | —  |     |    |    |    |
|   | 1.00 | PPI | SUTAN   | 5.00 |     |    | 100 | —  | 100 | —  |    |    |
|   | 5.00 | PPI | SUTAN   | 5.00 |     |    | 100 | —  | 100 | —  |    |    |
| 3 | 1.00 | IF  | VERNAM  | 1.00 |     |    | 70  | —  | 100 | —  |    |    |
|   | 5.00 | IF  | VERNAM  | 1.00 |     |    | 70  | —  | 100 | —  |    |    |
|   | 1.00 | IF  | VERNAM  | 1.25 |     |    | 70  | —  | 95  | —  |    |    |
|   | 5.00 | IF  | VERNAM  | 1.25 |     |    | 70  | —  | 95  | —  |    |    |
|   | 1.00 | PPI | VERNAM  | 1.25 |     |    | 85  | —  | 100 | —  |    |    |
|   | 5.00 | PPI | VERNAM  | 1.25 |     |    | 85  | —  | 100 | —  |    |    |
|   | 0.50 | PPI | VERNAM  | 1.25 | 100 | —  |     |    | 100 | —  |    |    |
|   | 1.00 | PPI | VERNAM  | 1.25 | 100 | —  |     |    | 100 | —  |    |    |
|   | 2.00 | PPI | VERNAM  | 1.25 | 100 | —  |     |    | 100 | —  |    |    |
|   | 1.00 | IF  | RO-NEET | 3.00 |     |    | 80  | —  |     |    | 95 | —  |
|   | 5.00 | IF  | RO-NEET | 3.00 |     |    | 80  | —  |     |    | 95 | —  |
|   | 5.00 | PES | LASSO   | 3.00 | 100 | —  | 100 | —  |     |    |    |    |
|   | 5.00 | PES | LASSO   | 4.00 | 100 | —  | 100 | —  |     |    |    |    |
| 4 | 1.00 | IF  | VERNAM  | 1.25 |     |    | 70  | —  | 95  | —  |    |    |
|   | 5.00 | IF  | VERNAM  | 1.25 |     |    | 70  | —  | 95  | —  |    |    |
|   | 0.50 | PPI | VERNAM  | 1.25 | 100 | —  |     |    | 100 | —  |    |    |
|   | 1.00 | PPI | VERNAM  | 1.25 | 100 | —  |     |    | 100 | —  |    |    |
|   | 2.00 | PPI | VERNAM  | 1.25 | 100 | —  |     |    | 100 | —  |    |    |
|   | 1.00 | PPI | VERNAM  | 5.00 | 95  | —  | 95  | —  |     |    |    |    |
|   | 5.00 | PPI | VERNAM  | 5.00 | 95  | —  | 95  | —  |     |    |    |    |
|   | 0.50 | PPI | EPTAM   | 5.00 | 100 | —  | 100 | —  |     |    |    |    |
|   | 5.00 | PPI | EPTAM   | 5.00 | 100 | —  | 100 | —  |     |    |    |    |
|   | 1.00 | PPI | SUTAN   | 6.00 |     |    |     |    | 100 | —  | 90 | —  |
|   | 5.00 | PPI | SUTAN   | 6.00 |     |    |     |    | 100 | —  | 90 | —  |
| 5 | 1.00 | IF  | VERNAM  | 1.00 | 70  | 60 | 70  | —  |     |    |    |    |
|   | 5.00 | IF  | VERNAM  | 1.00 | 70  | 60 | 70  | —  |     |    |    |    |
|   | 1.00 | IF  | VERNAM  | 5.00 | 100 | —  | 100 | —  |     |    |    |    |
|   | 5.00 | IF  | VERNAM  | 5.00 | 100 | —  | 100 | —  |     |    |    |    |
|   | 0.50 | PPI | VERNAM  | 6.00 | 100 | —  | 90  | —  |     |    |    |    |
|   | 1.00 | PPI | VERNAM  | 6.00 | 100 | —  | 90  | —  |     |    |    |    |
|   | 0.50 | PPI | VERNAM  | 7.00 | 100 | —  | 100 | —  |     |    |    |    |
|   | 1.00 | PPI | VERNAM  | 7.00 | 100 | —  | 100 | —  |     |    |    |    |
|   | 2.00 | PPI | VERNAM  | 7.00 | 100 | —  | 100 | —  |     |    |    |    |
| 6 | 1.00 | IF  | RO-NEET | 3.00 |     |    | 80  | —  |     |    | 95 | —  |
|   | 5.00 | IF  | RO-NEET | 3.00 |     |    | 80  | —  |     |    | 95 | 60 |
| 7 | 1.00 | IF  | VERNAM  | 6.00 | 100 | —  | 100 | —  |     |    |    |    |
|   | 5.00 | IF  | VERNAM  | 6.00 | 100 | —  | 100 | 95 |     |    |    |    |
|   | 1.00 | IF  | RO-NEET | 3.00 |     |    | 80  | —  |     |    | 95 | —  |
|   | 5.00 | IF  | RO-NEET | 3.00 |     |    | 80  | —  |     |    | 95 | —  |
| 8 | 1.00 | PPI | VERNAM  | 6.00 | 100 | —  | 100 | —  |     |    |    |    |
|   | 2.50 | PPI | VERNAM  | 6.00 | 100 | —  | 100 | —  |     |    |    |    |
|   | 5.00 | PPI | VERNAM  | 6.00 | 100 | —  | 100 | —  |     |    |    |    |
|   | 1.00 | PPI | VERNAM  | 6.00 | 85  | —  | 90  | —  |     |    |    |    |
|   | 5.00 | PPI | VERNAM  | 6.00 | 85  | —  | 90  | —  |     |    |    |    |
| 9 | 1.00 | PPI | VERNAM  | 6.00 | 85  | —  | 90  | —  |     |    |    |    |
|   | 5.00 | PPI | VERNAM  | 6.00 | 85  | —  | 90  | —  |     |    |    |    |
| 10| 1.00 | IF  | VERNAM  | 1.25 | 90  | —  |     |    | 100 | —  |    |    |
|   | 5.00 | IF  | VERNAM  | 1.25 | 90  | —  |     |    | 100 | —  |    |    |
|   | 0.50 | PPI | EPTAM   | 5.00 | 100 | —  | 100 | —  |     |    |    |    |
|   | 5.00 | PPI | EPTAM   | 5.00 | 100 | —  | 100 | —  |     |    |    |    |
|   | 1.00 | PPI | SUTAN   | 5.00 |     |    | 100 | —  | 100 | —  |    |    |
|   | 5.00 | PPI | SUTAN   | 5.00 |     |    | 100 | —  | 100 | —  |    |    |
| 11| 1.00 | PPI | VERNAM  | 6.00 | 85  | —  | 90  | —  |     |    |    |    |
|   | 5.00 | PPI | VERNAM  | 6.00 | 85  | —  | 90  | —  |     |    |    |    |
| 12| 1.00 | IF  | VERNAM  | 1.00 | 100 | —  |     |    | 100 | —  |    |    |
|   | 5.00 | IF  | VERNAM  | 1.00 | 100 | —  |     |    | 100 | —  |    |    |
|   | 1.00 | IF  | VERNAM  | 1.25 |     |    | 70  | —  | 100 | —  |    |    |
|   | 5.00 | IF  | VERNAM  | 1.25 |     |    | 70  | —  | 100 | —  |    |    |
|   | 1.00 | PPI | VERNAM  | 6.00 | 85  | —  | 90  | —  |     |    |    |    |
|   | 5.00 | PPI | VERNAM  | 6.00 | 85  | —  | 90  | —  |     |    |    |    |
|   | 0.50 | PPI | EPTAM   | 5.00 | 100 | —  | 100 | —  |     |    |    |    |
|   | 5.00 | PPI | EPTAM   | 5.00 | 100 | —  | 100 | —  |     |    |    |    |
| 13| 1.00 | IF  | VERNAM  | 1.00 | 75  | 40 |     |    |     |    | 95 | —  |
|   | 5.00 | IF  | VERNAM  | 1.00 | 75  | 40 |     |    |     |    | 95 | 60 |
|   | 1.00 | IF  | VERNAM  | 1.00 | 70  | 60 |     |    | 95  | —  |    |    |
|   | 5.00 | IF  | VERNAM  | 1.00 | 70  | 30 |     |    | 95  | —  |    |    |
|   | 1.00 | PPI | VERNAM  | 6.00 | 85  | —  | 90  | —  |     |    |    |    |
|   | 5.00 | PPI | VERNAM  | 6.00 | 85  | —  | 90  | —  |     |    |    |    |
|   | 0.50 | PPI | EPTAM   | 5.00 | 100 | —  | 100 | —  |     |    |    |    |
|   | 5.00 | PPI | EPTAM   | 5.00 | 100 | —  | 100 | —  |     |    |    |    |
|   | 1.00 | IF  | RO-NEET | 3.00 | 85  | —  |     |    |     |    | 95 | —  |
|   | 5.00 | IF  | RO-NEET | 3.00 | 85  | 60 |     |    |     |    | 95 | —  |
|   | 1.00 | PPI | SUTAN   | 5.00 |     |    | 100 | —  | 100 | —  |    |    |
|   | 5.00 | PPI | SUTAN   | 5.00 |     |    | 100 | —  | 100 | —  |    |    |
| 14| 1.00 | IF  | VERNAM  | 1.25 | 85  | 60 |     |    |     |    |    |    |
|   | 5.00 | IF  | VERNAM  | 1.25 | 85  | 50 |     |    |     |    |    |    |
|   | 0.50 | PPI | EPTAM   | 5.00 | 100 | —  | 100 | —  |     |    |    |    |
|   | 5.00 | PPI | EPTAM   | 5.00 | 100 | —  | 100 | —  |     |    |    |    |
|   | 1.00 | PPI | SUTAN   | 5.00 |     |    | 100 | —  |     |    | 100| —  |

TABLE V-continued

| | | | | | | | | | | | | |
|---|---|---|---|---|---|---|---|---|---|---|---|---|
| | 5.00 | PPI | SUTAN | 5.00 | | | 100 | — | | | 100 | — |
| 15 | 1.00 | PPI | VERNAM | 1.25 | 97 | — | 97 | — | | | | |
| | 2.00 | PPI | VERNAM | 1.25 | 97 | — | 97 | — | | | | |
| | 5.00 | PPI | VERNAM | 1.25 | 97 | — | 97 | — | | | | |
| | 1.00 | IF | VERNAM | 1.70 | 60 | 50 | 60 | — | | | | |
| | 5.00 | IF | VERNAM | 1.70 | 60 | 30 | 60 | — | | | | |
| | 1.00 | IF | VERNAM | 5.00 | 100 | — | 90 | — | | | | |
| | 5.00 | IF | VERNAM | 5.00 | 100 | — | 90 | — | | | | |
| | 0.50 | PPI | EPTAM | 5.00 | 100 | — | 100 | — | | | | |
| | 5.00 | PPI | EPTAM | 5.00 | 100 | — | 100 | — | | | | |
| 16 | 1.00 | IF | VERNAM | 1.00 | | | 70 | — | 100 | — | | |
| | 5.00 | IF | VERNAM | 1.00 | | | 70 | — | 100 | — | | |
| | 1.00 | IF | VERNAM | 1.00 | 100 | — | | | 100 | — | | |
| | 5.00 | IF | VERNAM | 1.00 | 100 | — | | | 100 | — | | |
| | 1.00 | PPI | VERNAM | 6.00 | 85 | — | 90 | — | | | | |
| | 5.00 | PPI | VERNAM | 6.00 | 85 | — | 90 | — | | | | |
| 17 | 1.00 | IF | VERNAM | 1.00 | | | | | 70 | — | 100 | — |
| | 5.00 | IF | VERNAM | 1.00 | | | | | 70 | — | 100 | — |
| 19 | 1.00 | PPI | VERNAM | 5.00 | 95 | — | 95 | — | | | | |
| | 5.00 | PPI | VERNAM | 5.00 | 95 | — | 95 | — | | | | |
| | 0.50 | PPI | EPTAM | 5.00 | 100 | — | 100 | — | | | | |
| | 5.00 | PPI | EPTAM | 5.00 | 100 | — | 100 | — | | | | |
| 20 | 0.50 | PPI | VERNAM | 6.00 | 100 | — | 100 | — | | | | |
| | 5.00 | PPI | VERNAM | 6.00 | 100 | — | 100 | — | | | | |
| | 0.50 | PPI | VERNAM | 6.00 | 98 | — | 100 | — | | | | |
| | 5.00 | PPI | VERNAM | 6.00 | 98 | — | 100 | — | | | | |
| | 0.50 | PPI | EPTAM | 5.00 | 100 | — | 100 | — | | | | |
| | 5.00 | PPI | EPTAM | 5.00 | 100 | — | 100 | — | | | | |
| | 1.00 | IF | SUTAN | 5.00 | | | | | 100 | — | 100 | — |
| | 5.00 | IF | SUTAN | 5.00 | | | | | 100 | — | 100 | — |
| 21 | 0.50 | PPI | EPTAM | 5.00 | 100 | — | 100 | — | | | | |
| | 5.00 | PPI | EPTAM | 5.00 | 100 | — | 100 | — | | | | |
| | 1/20 | PPI | EPTAM | 6.00 | 100 | — | 100 | — | | | | |
| | 1/40 | PPI | EPTAM | 6.00 | 100 | — | 100 | — | | | | |
| | 1/400 | PPI | EPTAM | 6.00 | 100 | — | 100 | — | | | | |
| | 1.00 | IF | RO-NEET | 3.00 | | | | | 95 | — | 95 | — |
| | 5.00 | IF | RO-NEET | 3.00 | | | | | 95 | — | 95 | — |
| 22 | 1.00 | PPI | VERNAM | 1.00 | 100 | — | 100 | — | | | | |
| | 5.00 | PPI | VERNAM | 1.00 | 100 | — | 100 | — | | | | |
| | 1.00 | IF | VERNAM | 1.25 | 95 | — | 80 | — | | | | |
| | 5.00 | IF | VERNAM | 1.25 | 95 | — | 80 | — | | | | |
| | 1.00 | IF | VERNAM | 1.25 | 95 | — | 80 | — | | | | |
| | 5.00 | IF | VERNAM | 1.25 | 95 | — | 80 | — | | | | |
| | 1.00 | IF | VERNAM | 1.25 | 90 | — | 85 | — | | | | |
| | 5.00 | IF | VERNAM | 1.25 | 90 | — | 85 | — | | | | |
| | 1.00 | IF | RO-NEET | 3.00 | 90 | — | 90 | — | | | | |
| | 5.00 | IF | RO-NEET | 3.00 | 90 | — | 90 | — | | | | |
| 23 | 1.00 | IF | VERNAM | 6.00 | 100 | — | 100 | — | | | | |
| | 5.00 | IF | VERNAM | 6.00 | 100 | — | 100 | — | | | | |
| | 0.50 | PPI | VERNAM | 7.00 | 100 | — | 100 | — | | | | |
| | 1.00 | PPI | VERNAM | 7.00 | 100 | — | 100 | — | | | | |
| | 2.00 | PPI | VERNAM | 7.00 | 100 | — | 100 | — | | | | |
| | 0.50 | PPI | VERNAM | 7.00 | 100 | — | 100 | — | | | | |
| | 1.00 | PPI | VERNAM | 7.00 | 100 | — | 100 | — | | | | |
| | 2.00 | PPI | VERNAM | 7.00 | 100 | — | 100 | — | | | | |
| 24 | 1.00 | PPI | VERNAM | 6.00 | 100 | — | 100 | — | | | | |
| | 2.50 | PPI | VERNAM | 6.00 | 100 | — | 100 | — | | | | |
| | 5.00 | PPI | VERNAM | 6.00 | 100 | — | 100 | — | | | | |
| | 1.00 | PPI | VERNAM | 6.00 | 85 | — | 90 | — | | | | |
| | 5.00 | PPI | VERNAM | 6.00 | 85 | — | 90 | — | | | | |
| 25 | 1.00 | PPI | VERNAM | 6.00 | 85 | — | 90 | — | | | | |
| | 5.00 | PPI | VERNAM | 6.00 | 85 | — | 90 | — | | | | |
| 26 | 1.00 | PPI | VERNAM | 6.00 | 85 | — | 90 | — | | | | |
| | 5.00 | PPI | VERNAM | 6.00 | 85 | — | 90 | — | | | | |
| | 0.50 | PPI | EPTAM | 5.00 | 100 | — | 100 | — | | | | |
| | 5.00 | PPI | EPTAM | 5.00 | 100 | — | 100 | — | | | | |
| 27 | 0.50 | PPI | EPTAM | 5.00 | 100 | — | 100 | — | | | | |
| | 5.00 | PPI | EPTAM | 5.00 | 100 | — | 100 | — | | | | |
| 28 | 1.00 | PPI | VERNAM | 1.25 | | | 85 | — | 100 | — | | |
| " | 5.00 | PPI | VERNAM | 1.25 | | | 85 | — | 100 | — | | |
| | 1.00 | PPI | VERNAM | 1.00 | 95 | — | | | 100 | — | | |
| | 5.00 | PPI | VERNAM | 1.00 | 95 | — | | | 100 | — | | |
| | 0.25 | PPI | VERNAM | 1.25 | | | 70 | — | 100 | — | | |
| | 0.50 | PPI | VERNAM | 1.25 | | | 70 | — | 100 | — | | |
| | 1.00 | PPI | VERNAM | 1.25 | | | 70 | — | 100 | — | | |
| | 1.00 | PPI | VERNAM | 6.00 | 85 | — | 90 | — | | | | |
| | 5.00 | PPI | VERNAM | 6.00 | 85 | — | 90 | — | | | | |
| | 1.00 | IF | RO-NEET | 4.00 | | | 80 | — | | | 100 | — |
| | 5.00 | IF | RO-NEET | 4.00 | | | 80 | — | | | 100 | — |
| | 1.00 | PPI | RO-NEET | 3.00 | 100 | — | | | | | 100 | — |
| | 5.00 | PPI | RO-NEET | 3.00 | 100 | — | | | | | 100 | — |
| | 1.00 | PPI | SUTAN | 5.00 | | | 100 | — | 100 | — | | |

TABLE V-continued

| | | | | | | | | | | | | | | |
|---|---|---|---|---|---|---|---|---|---|---|---|---|---|---|
| | 5.00 | PPI | SUTAN | 5.00 | | | 100 | — | | | 100 | — | | |
| 29 | 1.00 | IF | VERNAM | 1.00 | 70 | — | 60 | — | | | | | | |
| | 5.00 | IF | VERNAM | 1.00 | 70 | 50 | 60 | 50 | | | | | | |
| | 1.00 | PPI | VERNAM | 1.25 | | | 85 | — | 100 | — | | | | |
| | 5.00 | PPI | VERNAM | 1.25 | | | 85 | — | 100 | — | | | | |
| | 1.00 | IF | VERNAM | 1.70 | 60 | 30 | 60 | — | | | | | | |
| | 5.00 | IF | VERNAM | 1.70 | 60 | — | 60 | — | | | | | | |
| | 1.00 | PPI | VERNAM | 6.00 | 85 | — | 90 | — | | | | | | |
| | 5.00 | PPI | VERNAM | 6.00 | 85 | — | 90 | — | | | | | | |
| | 5.00 | PES | LASSO | 3.00 | 100 | — | 100 | — | | | | | | |
| | 5.00 | PES | LASSO | 4.00 | 100 | — | 100 | — | | | | | | |
| 30 | 1.00 | IF | VERNAM | 1.00 | | | 50 | — | 100 | — | | | | |
| | 5.00 | IF | VERNAM | 1.00 | | | 50 | — | 100 | — | | | | |
| | 1.00 | IF | VERNAM | 1.25 | 60 | — | | | 100 | — | | | | |
| | 5.00 | IF | VERNAM | 1.25 | 60 | 30 | | | 100 | — | | | | |
| | 0.50 | PPI | VERNAM | 1.25 | 90 | — | 90 | — | | | | | | |
| | 1.00 | PPI | VERNAM | 1.25 | 90 | — | 90 | — | | | | | | |
| | 2.00 | PPI | VERNAM | 1.25 | 90 | — | 90 | — | | | | | | |
| | 1.00 | PPI | EPTAM | 5.00 | 100 | — | 100 | — | | | | | | |
| | 5.00 | PPI | EPTAM | 5.00 | 100 | — | 100 | — | | | | | | |
| | 1.00 | PPI | SUTAN | 5.00 | | | | | | | 100 | — | 90 | — |
| | 5.00 | PPI | SUTAN | 5.00 | | | | | | | 100 | — | 90 | — |
| | 1.00 | PPI | SUTAN | 6.00 | 98 | 60 | 98 | — | | | | | | |
| | 5.00 | PPI | SUTAN | 6.00 | 98 | 75 | 98 | — | | | | | | |
| | 0.50 | PPI | SUTAN | 6.00 | 100 | — | | | 100 | — | | | | |
| | 1.00 | PPI | SUTAN | 6.00 | 100 | — | | | 100 | — | | | | |
| | 2.00 | PPI | SUTAN | 6.00 | 100 | — | | | 100 | — | | | | |
| 31 | 1.00 | IF | VERNAM | 1.00 | | | 70 | — | 100 | — | | | | |
| | 5.00 | IF | VERNAM | 1.00 | | | 70 | — | 100 | — | | | | |
| | 1.00 | PPI | VERNAM | 6.00 | 85 | — | 90 | — | | | | | | |
| | 5.00 | PPI | VERNAM | 6.00 | 85 | — | 90 | — | | | | | | |
| | 1.00 | PPI | SUTAN | 5.00 | | | 100 | — | 100 | — | | | | |
| | 5.00 | PPI | SUTAN | 5.00 | | | 100 | — | 100 | — | | | | |
| 32 | 0.50 | PPI | EPTAM | 5.00 | 100 | — | 100 | — | | | | | | |
| | 5.00 | PPI | EPTAM | 5.00 | 100 | — | 100 | — | | | | | | |
| 33 | 1.00 | IF | VERNAM | 1.25 | | | 70 | — | 100 | — | | | | |
| | 5.00 | IF | VERNAM | 1.25 | | | 70 | — | 100 | — | | | | |
| 34 | 1.00 | PPI | VERNAM | 1.00 | 95 | — | | | 100 | — | | | | |
| | 5.00 | PPI | VERNAM | 1.00 | 95 | — | | | 100 | — | | | | |
| | 1.00 | PPI | VERNAM | 1.25 | | | 85 | — | 100 | — | | | | |
| | 5.00 | PPI | VERNAM | 1.25 | | | 85 | — | 100 | — | | | | |
| | 0.25 | PPI | VERNAM | 1.25 | | | 70 | — | 100 | — | | | | |
| | 0.50 | PPI | VERNAM | 1.25 | | | 70 | — | 100 | — | | | | |
| | 1.00 | PPI | VERNAM | 1.25 | | | 70 | — | 100 | — | | | | |
| | 1.00 | PPI | RO-NEET | 3.00 | 100 | — | | | | | 100 | — | | |
| | 5.00 | PPI | RO-NEET | 3.00 | 100 | — | | | | | 100 | — | | |
| 36 | 1.00 | IF | VERNAM | 1.25 | | | 70 | — | 100 | — | | | | |
| | 5.00 | IF | VERNAM | 1.25 | | | 70 | — | 100 | — | | | | |
| | 1.00 | IF | VERNAM | 6.00 | 100 | — | 100 | — | | | | | | |
| | 5.00 | IF | VERNAM | 6.00 | 100 | — | 100 | — | | | | | | |
| | 0.50 | PPI | VERNAM | 7.00 | 100 | — | 100 | — | | | | | | |
| | 1.00 | PPI | VERNAM | 7.00 | 100 | — | 100 | — | | | | | | |
| | 2.00 | PPI | VERNAM | 7.00 | 100 | — | 100 | — | | | | | | |
| 38 | 0.50 | PPI | VERNAM | 6.00 | 100 | — | 100 | — | | | | | | |
| | 2.00 | PPI | VERNAM | 6.00 | 100 | — | 100 | — | | | | | | |
| | 0.50 | PPI | VERNAM | 6.00 | 98 | — | 100 | — | | | | | | |
| | 2.00 | PPI | VERNAM | 6.00 | 98 | — | 100 | — | | | | | | |
| 39 | 0.50 | PPI | VERNAM | 6.00 | 98 | — | 100 | — | | | | | | |
| | 2.00 | PPI | VERNAM | 6.00 | 98 | — | 100 | — | | | | | | |
| 40 | 0.50 | PPI | VERNAM | 6.00 | 100 | — | 100 | — | | | | | | |
| | 2.00 | PPI | VERNAM | 6.00 | 100 | — | 100 | — | | | | | | |
| | 0.50 | PPI | VERNAM | 6.00 | 98 | — | 100 | — | | | | | | |
| | 2.00 | PPI | VERNAM | 6.00 | 98 | — | 100 | — | | | | | | |
| | 0.50 | PPI | EPTAM | 5.00 | | | 100 | — | 100 | — | | | | |
| | 5.00 | PPI | EPTAM | 5.00 | | | 100 | — | 100 | — | | | | |
| 43 | 1.00 | PPI | VERNAM | 5.00 | 95 | — | 95 | — | | | | | | |
| | 5.00 | PPI | VERNAM | 5.00 | 95 | — | 95 | — | | | | | | |
| 44 | 1.00 | IF | VERNAM | 5.00 | 100 | — | 90 | — | | | | | | |
| | 5.00 | IF | VERNAM | 5.00 | 100 | — | 90 | — | | | | | | |
| | 0.50 | PPI | EPTAM | 5.00 | 100 | — | 100 | — | | | | | | |
| | 5.00 | PPI | EPTAM | 5.00 | 100 | — | 100 | — | | | | | | |
| 45 | 1.00 | IF | VERNAM | 1.00 | 100 | — | | | 100 | — | | | | |
| | 5.00 | IF | VERNAM | 1.00 | 100 | — | | | 100 | — | | | | |
| | 1.00 | IF | VERNAM | 1.25 | | | 70 | — | 100 | — | | | | |
| | 5.00 | IF | VERNAM | 1.25 | | | 70 | — | 100 | — | | | | |
| 46 | 1.00 | IF | VERNAM | 1.00 | | | 60 | — | 100 | — | | | | |
| | 5.00 | IF | VERNAM | 1.00 | | | 60 | — | 100 | — | | | | |
| | 1.00 | IF | VERNAM | 1.25 | 95 | — | 80 | — | | | | | | |
| | 5.00 | IF | VERNAM | 1.25 | 95 | — | 80 | — | | | | | | |
| 47 | 1.00 | PPI | VERNAM | 6.00 | 85 | — | 90 | — | | | | | | |
| | 5.00 | PPI | VERNAM | 6.00 | 85 | — | 90 | — | | | | | | |
| 48 | 1.00 | PPI | VERNAM | 6.00 | 85 | — | 90 | — | | | | | | |

TABLE V-continued

| Cmpd. No. | Antidote Rate | Method | Herbicide Name | Rate | Watergrass U | T | Foxtail U | T | Wild Oat U | T | Johnsongrass U | T | Shattercane U | T | Nutsedge U | T |
|---|---|---|---|---|---|---|---|---|---|---|---|---|---|---|---|---|
|  | 5.00 | PPI | VERNAM | 6.00 | 85 | — | 90 | — |  |  |  |  |  |  |  |  |
|  | 1.00 | PPI | SUTAN | 5.00 |  |  | 100 | — |  |  | 100 | — |  |  |  |  |
|  | 5.00 | PPI | SUTAN | 5.00 |  |  | 100 | — |  |  | 100 | — |  |  |  |  |
| 49 | 1.00 | PPI | VERNAM | 1.00 | 95 | — |  |  | 100 | — |  |  |  |  |  |  |
|  | 5.00 | PPI | VERNAM | 1.00 | 95 | — |  |  | 100 | — |  |  |  |  |  |  |
|  | 1.00 | PPI | VERNAM | 1.25 |  |  | 85 | — | 100 | — |  |  |  |  |  |  |
|  | 5.00 | PPI | VERNAM | 1.25 |  |  | 85 | — | 100 | — |  |  |  |  |  |  |
|  | 0.25 | PPI | VERNAM | 1.25 |  |  | 70 | — | 100 | — |  |  |  |  |  |  |
|  | 0.50 | PPI | VERNAM | 1.25 |  |  | 70 | — | 100 | — |  |  |  |  |  |  |
|  | 1.00 | PPI | VERNAM | 1.25 |  |  | 70 | — | 100 | — |  |  |  |  |  |  |
|  | 1.00 | PPI | VERNAM | 6.00 | 85 | — | 90 | — |  |  |  |  |  |  |  |  |
|  | 5.00 | PPI | VERNAM | 6.00 | 85 | — | 90 | — |  |  |  |  |  |  |  |  |
|  | 1.00 | IF | RO-NEET | 4.00 |  |  | 80 | — |  |  |  |  | 100 | — |  |  |
|  | 5.00 | IF | RO-NEET | 4.00 |  |  | 80 | — |  |  |  |  | 100 | — |  |  |
|  | 1.00 | PPI | RO-NEET | 3.00 | 100 | — |  |  |  |  |  |  | 100 | — |  |  |
|  | 5.00 | PPI | RO-NEET | 3.00 | 100 | — |  |  |  |  |  |  | 100 | — |  |  |
|  | 0.25 | PPI | RO-NEET | 3.00 | 80 | — |  |  |  |  |  |  | 95 | — |  |  |
|  | 0.50 | PPI | RO-NEET | 3.00 | 80 | — |  |  |  |  |  |  | 95 | — |  |  |
|  | 1.00 | PPI | RO-NEET | 3.00 | 80 | — |  |  |  |  |  |  | 95 | — |  |  |
| 50 | 1.00 | IF | VERNAM | 1.00 | 70 | 60 | 60 | — |  |  |  |  |  |  |  |  |
|  | 5.00 | IF | VERNAM | 1.00 | 70 | — | 60 | — |  |  |  |  |  |  |  |  |
|  | 1.00 | IF | VERNAM | 1.70 | 60 | — | 60 | — |  |  |  |  |  |  |  |  |
|  | 5.00 | IF | VERNAM | 1.70 | 60 | 40 | 60 | — |  |  |  |  |  |  |  |  |
|  | 1.00 | PPI | VERNAM | 6.00 | 85 | — | 90 | — |  |  |  |  |  |  |  |  |
|  | 5.00 | PPI | VERNAM | 6.00 | 85 | — | 90 | — |  |  |  |  |  |  |  |  |
| 51 | 1.00 | PPI | VERNAM | 6.00 | 85 | — | 90 | — |  |  |  |  |  |  |  |  |
|  | 5.00 | PPI | VERNAM | 6.00 | 85 | — | 90 | — |  |  |  |  |  |  |  |  |
| 52 | 1.00 | IF | VERNAM | 1.00 | 70 | 50 | 60 | 40 |  |  |  |  |  |  |  |  |
|  | 5.00 | IF | VERNAM | 1.00 | 70 | 60 | 60 | — |  |  |  |  |  |  |  |  |
|  | 1.00 | PPI | VERNAM | 6.00 | 85 | — | 90 | — |  |  |  |  |  |  |  |  |
|  | 5.00 | PPI | VERNAM | 6.00 | 85 | — | 90 | — |  |  |  |  |  |  |  |  |
|  | 5.00 | PES | LASSO | 3.00 | 100 | — | 100 | — |  |  |  |  |  |  |  |  |
|  | 5.00 | PES | LASSO | 4.00 | 100 | — | 100 | — |  |  |  |  |  |  |  |  |
| 53 | 1.00 | IF | VERNAM | 5.00 | 95 | — | 95 | — |  |  |  |  |  |  |  |  |
|  | 5.00 | IF | VERNAM | 5.00 | 95 | — | 95 | — |  |  |  |  |  |  |  |  |
|  | 1.00 | IF | RO-NEET | 3.00 |  |  | 80 | — |  |  |  |  | 95 | — |  |  |
|  | 5.00 | IF | RO-NEET | 3.00 |  |  | 80 | — |  |  |  |  | 95 | — |  |  |
| 54 | 1.00 | PPI | VERNAM | 1.25 |  |  | 70 | — | 100 | — |  |  |  |  |  |  |
|  | 5.00 | PPI | VERNAM | 1.25 |  |  | 70 | — | 100 | — |  |  |  |  |  |  |
| 56 | 1.00 | IF | RO-NEET | 3.00 |  |  | 80 | — |  |  |  |  | 95 | — |  |  |
|  | 5.00 | IF | RO-NEET | 3.00 |  |  | 80 | — |  |  |  |  | 95 | — |  |  |
| 58 | 1.00 | IF | RO-NEET | 3.00 |  |  | 80 | — |  |  |  |  | 95 | — |  |  |
|  | 5.00 | IF | RO-NEET | 3.00 |  |  | 80 | — |  |  |  |  | 95 | — |  |  |

Test Results

The compounds and compositions of this invention show good antidotal activity for a variety of crops. They were effective by all methods of application.

Formulations

The compounds and compositions can be formulated in the same manner in which herbicides are generally formulated. The object of the formulation is to apply the compounds and compositions to the locus where control is desired by a conventional method. The "locus" may include soil, seeds, seedlings, and vegetation.

The active herbicidal ingredient of a formulation will generally be such that its application rate will be within the range of 0.01 to 50 lb/A (0.0112 to 56 k/ha). The antidote compound which may be formulated separately or together with the herbicide will generally comprise about 0.001 to about 30 parts by weight of the herbicide.

Formulations will generally contain several additives. Among these are some inert ingredients, diluent carriers, organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surfact active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omegasubstituted polyethylene glycols of relatively long chain length. A list of surface active agents suitable for use in agriculture formulations can be found in Wade Van Valkenburg, *Pesticide Formulations,* (Marcel Dekker, Inc., N.Y., 1973) at pages 79-84.

Granules comprise the herbicidal composition impregnated on a particulate inert carrier having a particle size of about 1 to 2 millimeters in diameter. The granules can be made by apraying a solution of the active ingredient in a volatile solvent onto the granule carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

I claim:

1. A compound of the formula

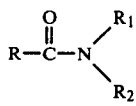

in which

R is 1-4 carbon haloalkyl wherein halo is bromo or chloro:

$R_1$ is selected from the group consisting of hydrogen and 1-4 carbon alkyl; and $R_2$ is selected from the group consisting of 5-12 carbon cyanoalkylcycloalkyl, 5-12 carbon cyanocycloalkyl, and 3-6 carbon cyanoalkylalkoxy.

2. A compound acoording to claim 1 in which R is 1,2-dibromoethyl, $R_1$ is hydrogen and $R_2$ is 1-cyano-1-methyl-2-methoxyethyl.

3. A compound according to claim 1 in which R is haloalkyl, $R_1$ is hydrogen and $R_2$ is 1-cyano-1-cyclopropylethyl.

4. A compound according to claim 3 in which R is chloromethyl.

5. A compound according to claim 3 in which R is dichloromethyl.

6. A compound according to claim 3 in which R is 1,2-dibromoethyl.

7. A compound according to claim 1 in which R is haloalkyl, $R_1$ is methyl, and $R_2$ is 1-cyanocyclopentyl.

8. A compound according to claim 7 in which R is chloromethyl.

9. A compound according to claim 7 in which R is bromomethyl.

10. A compound according to claim 7 in which R is dichloromethyl.

11. A compound according to claim 7 in which R is trichloromethyl.

12. A compound according to claim 7 in which R is 1,2-dibromoethyl.

13. A compound according to claim 1 in which R is haloalkyl, $R_1$ is hydrogen and $R_2$ is 1-cyanocyclopentyl.

14. A compound according to claim 13 in which R is 1,2-dichloroethyl.

15. A compound according to claim 13 in which R is dichloromethyl.

16. A compound according to claim 13 in which R is 1,2-dibromoethyl.

17. A compound according to claim 13 in which R is 1,2-dibromopropyl.

18. A compound according to claim 1 in which R is haloalkyl, $R_1$ is hydrogen and $R_2$ is 1-cyclopentylacetonitrilo.

19. A compound according to claim 18 in which R is chloromethyl.

20. A compound according to claim 18 in which R is dichloromethyl.

21. A compound according to claim 1 in which R is dichloromethyl, $R_1$ is hydrogen and $R_2$ is 1-methyl-1-cyclopentylacetonitrilo.

22. A compound according to claim 1 in which R is dichloromethyl, $R_1$ is methyl and $R_2$ is 1-cyanocyclohexyl.

23. A compound according to claim 1 in which R is haloalkyl, $R_1$ is hydrogen and $R_2$ is 1-cyanocyclohexyl.

24. A compound according to claim 23 in which R is chloromethyl.

25. A compound according to claim 23 in which R is dichloromethyl.

26. A compound according to claim 23 in which R is 1,2-dibromoethyl.

27. A compound according to claim 1 in which R is dichloromethyl, $R_1$ is hydrogen and $R_2$ is (1-cyano-1-cyclohexyl) ethyl.

28. A compound according to claim 1 in which R is haloalkyl, $R_1$ is hydrogen and $R_2$ is 1-cyano-4-methylcyclohexyl.

29. A compound according to claim 28 in which R is dichloromethyl.

30. A compound according to claim 28 in which R is 2-bromopropyl.

31. A compound according to claim 28 in which R is 1,2-dichloroethyl.

32. A compound according to claim 28 in which R is 1,2-dibromoethyl.

33. A compound according to claim 28 in which R is 1,1,2-trichloroethyl.

34. A compound according to claim 1 in which R is dichloromethyl, $R_1$ is hydrogen and $R_2$ is 1-cyano-4-ethylcyclohexyl.

35. A compound according to claim 1 in which R is dichloromethyl, $R_1$ is hydrogen and $R_2$ is 1-cyano-4-t-butylcyclohexyl.

36. A compound according to claim 1 in which R is chloromethyl, $R_1$ is hydrogen and $R_2$ is 1-cyano-4-neopentylcyclohexyl.

37. A compound according to claim 1 in which R is haloalkyl, $R_1$ is hydrogen and $R_2$ is 1-cyanocyclooctyl.

38. A compound according to claim 37 in which R is dichloromethyl.

39. A compound according to claim 37 in which R is 1,2-dibromoethyl.

* * * * *